US007972824B2

(12) United States Patent
Simpson et al.

(10) Patent No.: US 7,972,824 B2
(45) Date of Patent: Jul. 5, 2011

(54) MICROBIAL FERMENTATION OF GASEOUS SUBSTRATES TO PRODUCE ALCOHOLS

(75) Inventors: Sean Dennis Simpson, Auckland (NZ); Richard Llewellyn Sydney Forster, Pukekohe (NZ); Matthew Rowe, Arvada, CO (US)

(73) Assignee: LanzaTech New Zealand Limited, Auckland (NZ)

( * ) Notice: Subject to any disclaimer, the term of this patent is extended or adjusted under 35 U.S.C. 154(b) by 141 days.

(21) Appl. No.: 12/296,300

(22) PCT Filed: Apr. 5, 2007

(86) PCT No.: PCT/NZ2007/000072
§ 371 (c)(1),
(2), (4) Date: Apr. 17, 2009

(87) PCT Pub. No.: WO2007/117157
PCT Pub. Date: Oct. 18, 2007

(65) Prior Publication Data
US 2009/0203100 A1    Aug. 13, 2009

(30) Foreign Application Priority Data
Apr. 7, 2006    (NZ) ........................................ 546496

(51) Int. Cl.
*C12P 7/02*    (2006.01)
*C12P 7/06*    (2006.01)
*C12P 3/00*    (2006.01)

(52) U.S. Cl. ......................... 435/155; 435/161; 435/168
(58) Field of Classification Search .......................... None
See application file for complete search history.

(56) References Cited

U.S. PATENT DOCUMENTS

| | | |
|---|---|---|
| 4,851,344 A | 7/1989 | Simon et al. |
| 5,173,429 A | 12/1992 | Gaddy et al. |
| 5,593,886 A | 1/1997 | Gaddy |
| 5,753,474 A | 5/1998 | Ramey |
| 5,807,722 A | 9/1998 | Gaddy |
| 5,821,111 A | 10/1998 | Grady et al. |
| 6,136,577 A | 10/2000 | Gaddy |
| 6,306,638 B1 | 10/2001 | Yang et al. |
| 6,340,581 B1 | 1/2002 | Gaddy |
| 6,368,819 B1 | 4/2002 | Gaddy et al. |
| 6,753,710 B2 | 6/2004 | Doberenz |
| RE39,175 E | 7/2006 | Gaddy et al. |
| 7,196,218 B2 | 3/2007 | Gaddy et al. |
| 7,285,402 B2 | 10/2007 | Gaddy et al. |
| 2003/0211585 A1 | 11/2003 | Gaddy et al. |
| 2006/0051848 A1 | 3/2006 | Nishio et al. |
| 2007/0275447 A1 | 11/2007 | Lewis et al. |

FOREIGN PATENT DOCUMENTS

| | | |
|---|---|---|
| EP | 0 146 075 | 8/1989 |
| EP | 0 125 983 | 1/1990 |
| WO | 00/68407 | 11/2000 |
| WO | WO 00/68407 | 11/2000 |
| WO | 02/08438 | 1/2002 |
| WO | WO 02/08438 | 1/2002 |
| WO | WO 2007/117157 | 10/2007 |
| WO | WO 2008/028055 | 3/2008 |
| WO | WO 2008/154301 | 12/2008 |
| WO | WO 2009/020747 | 2/2009 |

OTHER PUBLICATIONS

Duncan, Sylvia H, et al.. "Contribution of acetate to butyrate formation by human faecal bacteria." 2004. British Journal of Nutrition, pp. 915-923.
Qureshi, Nasib, et al. "High-Productivity Continuous Biofilm Reactor for Butanol Production." Applied Biochemistry and Biotechnology, vol. 113-116, 2004. pp. 713-721.
Huang, Wei-Cho, et al. "Effects of Butyrate Uptake and Long-term Stability of a Fibrous Bed Bioreactor on Continuious ABE Fermentation by *Clostridium acetobutylicum*." 26 pages.
Chen, Chih-Kuang, et al. "Effect of Acetate on Molecular and Physiological Aspects of *Clostridium beijerinckii* NCIMB 8052 Solvent Production and Strain Degeneration." 1999. Applied and Environmental Microbiology, Feb. 1999, vol. 65, No. 2, pp. 499-505.
Ragsdale, Stephen. "Life with Carbon Monoxide." 2004. Critical Reviews in Biochemistry and Molecular Biology, pp. 165-195.
Henstra, Anne M. "Microbiology of synthesis gas fermentation for biofuel production." 2007. ScienceDirect (www.sciencedirect.com) pp. 200-206.
Phillips et al. "Synthesis gas as substrate for the biological production of fuels and chemicals", 1994. Applied Biochemistry and Biotechnology, 45(1), pp. 145-157.
Abrini et al. "*Clostridium autoethanogenum*, sp. Nov., an anaerobic bacterium that produces ethanol from carbon monoxide", 1994. Archives of Microbiology, 161(4), pp. 345-351.

*Primary Examiner* — Herbert J. Lilling
(74) *Attorney, Agent, or Firm* — Occhiuti Rohlicek & Tsao LLP

(57) ABSTRACT

The present invention relates to methods for increasing the efficiency of anaerobic fermentation processes (1) that produce acetate as a by-product in addition to a desired product, and (2) that can utilize hydrogen and/or carbon dioxide in the fermentation. The method comprises the steps of converting acetate produced by the fermentation process into hydrogen gas and carbon dioxide gas, and utilizing hydrogen gas and/or carbon dioxide gas obtained from the acetate conversion in the anaerobic fermentation process. In particular aspects, the invention relates to processes of producing alcohols, particularly ethanol.

15 Claims, 9 Drawing Sheets

MICROBIAL FERMENTATION OF GASEOUS SUBSTRATES TO PRODUCE ALCOHOLS

CROSS-REFERENCE TO RELATED APPLICATIONS

This application is the National Stage of International Application No. PCT/NZ2007/000072, filed on Apr. 5, 2007, which claims the priority of New Zealand Application No. 546496, filed on Apr. 7, 2006. The contents of both applications are hereby incorporated by reference in their entirety.

FIELD OF THE INVENTION

This invention relates generally to methods for increasing the efficiency of processes of producing products by microbial fermentation of gases. It more particularly relates to processes of producing ethanol by microbial fermentation of gaseous substrates containing carbon monoxide.

BACKGROUND OF THE INVENTION

Ethanol is rapidly becoming a major hydrogen-rich liquid transport fuel around the world. Worldwide consumption of ethanol in 2002 was an estimated 10.8 billion gallons. The global market for the fuel ethanol industry has also been predicted to grow sharply in future, due to an increased interest in ethanol in Europe, Japan, the USA and several developing nations.

For example, in the USA, ethanol is used to produce E10, a 10% mixture of ethanol in gasoline. In E10 blends the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, or as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

CO is a major free energy-rich by-product of the incomplete combustion of organic materials such as coal or oil and oil derived products. For example, the steel industry in Australia is reported to produce and release into the atmosphere over 500,000 tonnes of CO annually.

It has long been recognised that catalytic processes may be used to convert gases consisting primarily of CO and/or CO and hydrogen ($H_2$) into a variety of fuels and chemicals. However, micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as their sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Aribini et al, Archives of Microbiology 161, pp 345-351 (1994)).

However, ethanol production by micro-organisms by fermentation of gases is always associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to Green House Gas emissions.

It is an object of the present invention to provide a process that goes at least some way towards overcoming the above disadvantages, or at least to provide the public with a useful choice.

SUMMARY OF THE INVENTION

In a first aspect, the present invention provides a method for increasing the efficiency of an anaerobic fermentation process (1) that produces acetate as a by-product in addition to a desired product, and (2) that can utilise hydrogen and/or carbon dioxide in the fermentation, the method comprising the steps of:
  (a) converting acetate produced by the fermentation process into hydrogen gas and carbon dioxide gas; and
  (b) utilising hydrogen gas and/or carbon dioxide gas obtained from step (a) in the anaerobic fermentation process.

In preferred embodiments, the desired product of the fermentation is an alcohol, such as ethanol.

In preferred embodiments, acetate is removed from the fermentation before the acetate is converted into $H_2$ and $CO_2$.

In preferred embodiments, step (b) comprises introducing either hydrogen gas or a mixture of hydrogen and carbon dioxide gases obtained from step (a) into the anaerobic fermentation process.

In preferred embodiments, the anaerobic fermentation process comprises fermenting a gaseous substrate comprising CO to produce ethanol and acetate.

In preferred embodiments, the acetate is converted to $H_2$ and $CO_2$ by microbial oxidation.

In a second aspect, the present invention provides a process for producing one or more alcohols from a gaseous substrate comprising CO, comprising the steps of:
(a) in a bioreactor, anaerobically fermenting the gaseous substrate to produce one or more alcohols and acetate;
(b) converting acetate obtained from step (a) into $H_2$ and $CO_2$ gases; and
(c) using $H_2$ and/or $CO_2$ obtained from step (b) as a co-substrate in the fermentation process.

In preferred embodiments, the one or more alcohols comprises ethanol.

In preferred embodiments, the anaerobic fermentation (a) is carried out by one of more strains of acetogenic bacteria, in a liquid nutrient medium.

In certain preferred embodiments, the acetogenic bacterium is selected from *Clostridium, Moorella* and *Carboxydothermus*. In one embodiment, the acetogenic bacterium is *Clostridium autoethanogenum*.

In certain preferred embodiments, acetate is removed from the bioreactor before converting the acetate into $H_2$ and $CO_2$, and step (c) includes introducing either $H_2$ or a mixture comprising $H_2$ and $CO_2$ gases obtained from the acetate conversion into the bioreactor during the fermentation process (a).

In certain preferred embodiments, step (b) comprises microbial oxidation of the acetate to produce $H_2$ and $CO_2$.

In certain preferred embodiments, step (a) is carried out in a first bioreactor and step (b) is carried out in a second bioreactor.

In certain preferred embodiments, the oxidation of acetate is carried out by one or more bacteria of the genus *Geobacter* or *Clostridium*. In one embodiment, the bacterium is *Geobacter sulfurreducens*.

In certain preferred embodiments, the microbial oxidation of acetate is carried out in a liquid nutrient medium containing a limiting concentration of an electron acceptor, preferably about 20 mM or less.

In certain preferred embodiments, the gaseous substrate comprises a gas obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing.

In one embodiment, the gaseous substrate may comprise a gas obtained from a steel mill.

In another embodiment, the gaseous substrate may comprise automobile exhaust fumes.

In certain preferred embodiments, the gaseous substrate contains less than about 15% $H_2$ by volume, such as less than about 10% $H_2$, such as less than about 5% $H_2$.

In certain preferred embodiments, the gaseous substrate comprises greater than about 70% CO by volume, such as about 70% CO to about 90% CO by volume.

In certain preferred embodiments, acetate and the one or more alcohols are both recovered from the bioreactor before converting the acetate into $H_2$ and $CO_2$.

In certain preferred embodiments, the recovering of ethanol and acetate comprises continuously removing a portion of fermentation broth from the bioreactor and recovering separately ethanol and acetate from the removed portion of the broth.

In certain preferred embodiments the recovery of ethanol and acetate includes passing the removed portion of the broth containing ethanol and acetate through a separation unit to separate bacterial cells from the ethanol and acetate, to produce a cell-free ethanol- and acetate-containing permeate, and returning the bacterial cells to the bioreactor.

In the above embodiments, the recovery of ethanol and acetate preferably includes first removing ethanol from the cell-free permeate followed by removing acetate from the cell-free permeate, then returning the cell-free permeate to the bioreactor.

In certain embodiments, the processes of the present invention are continuous processes.

In a further aspect, the present invention provides a process for producing ethanol, the process comprising anaerobically fermenting a gaseous substrate comprising CO using one or more strains of anaerobic acetogenic bacteria in a bioreactor, and recovering the ethanol produced, wherein the gaseous substrate comprises at least 70% CO by volume.

In certain preferred embodiments the gaseous substrate comprises from 70% CO to 95% CO by volume, such as from 75% CO to 90% CO by volume, such as from 80% to 90% CO by volume.

In certain preferred embodiments, the bacterium is of the genus *Clostridium*. In one embodiment, the bacterium is *Clostridium autoethanogenum*, having the identifying characteristics of the Deutsche Samlung von Mikroorganismen und Zellkulturen GmbH (DSMZ) deposit number DSMZ 10061.

In a further aspect, the present invention provides a method for reducing the total atmospheric carbon emissions from an industrial process, the method comprising:
(a) capturing CO-containing gas produced as a result of the industrial process, before the gas is released into the atmosphere;
(b) in a bioreactor, anaerobically fermenting the CO-containing gas to produce one or more alcohols and acetate;
(c) converting acetate obtained from step (a) into $H_2$ and $CO_2$ gases; and
(d) using $H_2$ and/or $CO_2$ obtained from step (b) as a co-substrate in the fermentation process.

In a further aspect, the present invention provides a method for reducing the amount of CO-containing gas released into the atmosphere by an industrial process, the method comprising:
(a) capturing CO-containing gas produced as a result of the industrial process, before the gas is released into the atmosphere;
(b) in a bioreactor, anaerobically fermenting the CO-containing gas to produce one or more alcohols and acetate;
(c) converting acetate obtained from step (a) into $H_2$ and $CO_2$ gases; and
(d) using $H_2$ and/or $CO_2$ obtained from step (b) as a co-substrate in the fermentation process.

In a further aspect, the present invention provides a method for utilising a CO-containing gas, the method comprising:
(a) in a bioreactor, anaerobically fermenting the CO-containing gas to produce one or more alcohols and acetate;
(b) converting acetate obtained from step (a) into $H_2$ and $CO_2$ gases; and
(c) using $H_2$ and/or $CO_2$ obtained from step (b) as a co-substrate in the fermentation process.

In a further aspect, the present invention provides a method for reducing the total atmospheric carbon emissions from an industrial process, the method comprising:
(a) capturing CO-containing gas, comprising at least 70% CO by volume and produced as a result of the industrial process, before the gas is released into the atmosphere, and (b) anaerobically fermenting the CO-containing gas using one or more strains of anaerobic acetogenic bacteria, to produce one or more alcohols.

In a further aspect, the present invention provides a method for reducing the amount of CO-containing gas released into the atmosphere by an industrial process, the process comprising:

(a) capturing CO-containing gas, comprising at least 70% CO by volume and produced as a result of the industrial process, before the gas is released into the atmosphere, and (b) anaerobically fermenting the CO-containing gas using one or more strains of anaerobic acetogenic bacteria, to produce one or more alcohols.

In a further aspect, the present invention provides a method for utilising a CO-containing gas comprising at least 70% CO by volume, the method comprising anaerobically fermenting the CO-containing gas using one or more strains of anaerobic acetogenic bacteria, to produce one or more alcohols.

Although the invention is broadly as defined above, it is not limited thereto and also includes embodiments of which the following description provides examples.

BRIEF DESCRIPTION OF THE DRAWINGS

The invention will now be described in more detail and with reference to the accompanying figures, in which.

DETAILED DESCRIPTION OF THE INVENTION

Figure 1:
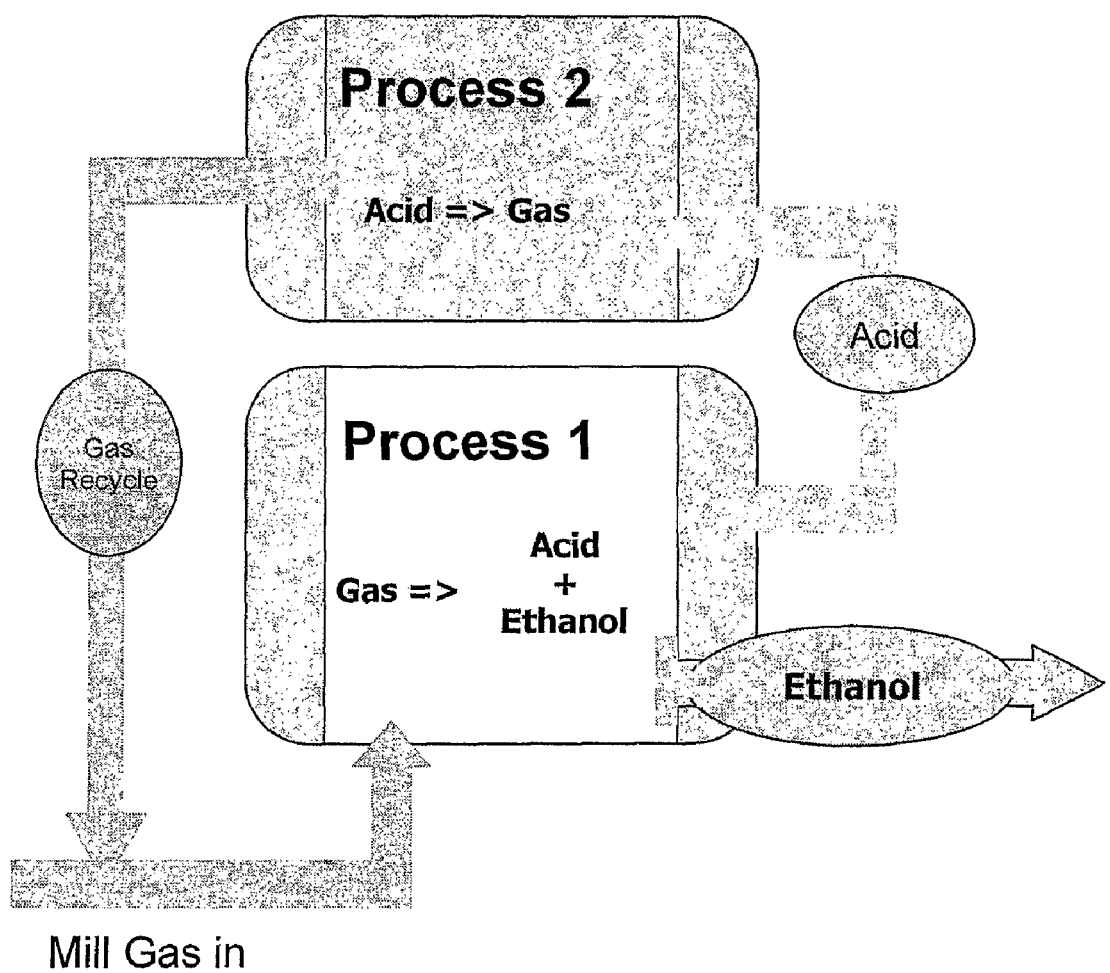
FIG. 1 is a schematic diagram illustrating an embodiment of a process of producing ethanol according to the present invention.

In broad terms, in one aspect the present invention relates to a method for increasing the efficiency of an anaerobic fermentation process that produces acetate as a by-product in addition to a desired product, preferably an alcohol, and that can utilise hydrogen and/or carbon dioxide as a co-substrate in the fermentation. The method includes the step of converting acetate produced by the fermentation process into hydrogen gas and carbon dioxide gas. The hydrogen and/or carbon dioxide gas is then utilised as a co-substrate by the micro-organisms performing the fermentation, thereby increasing the efficiency of the process.

Definitions

Unless otherwise defined, the following terms as used throughout this specification are defined as follows:

The terms "increasing the efficiency", "increased efficiency" and the like, when used in relation to a fermentation process, include, but are not limited to, increasing one or more of: the rate of growth of micro-organisms catalysing the fermentation, the volume of desired product (such as alcohols) produced per volume of substrate (such as carbon monoxide) consumed, the rate of production or level of production of the desired product, and the relative proportion of the desired product produced compared with other by-products of the fermentation.

The term "co-substrate" refers to a substance that while not being the primary energy and material source for product synthesis, can be utilised for product synthesis when added in addition to the primary substrate.

The term "acetate" includes both acetate salt alone and a mixture of molecular or free acetic acid and acetate salt, such as the mixture of acetate salt and free acetic acid present in a fermentation broth as described herein. The ratio of molecular acetic acid to acetate in the fermentation broth is dependent upon the pH of the system.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact.

The term "limiting concentration" means an initial concentration of a given component in a microbial fermentation medium that is sufficiently low to ensure that it will be depleted at an early stage in the fermentation.

In a particular aspect, the invention relates to a process of producing alcohols, more particularly ethanol, by anaerobic fermentation of gases containing carbon monoxide. In this aspect, the process involves recycling acetate that is produced as a by-product of a CO-to-ethanol fermentation process, by converting the acetate to $H_2$ and $CO_2$, thereby providing an immediate source of $H_2$ and/or $CO_2$ for the fermentation process. The availability of these gases, particularly $H_2$, in turn increases the efficiency with which available carbon from the gaseous substrate is converted into ethanol in the fermentation.

A process of the present invention is illustrated in general schematic form in FIG. 1, in which Reaction 1 is the conversion of CO-containing gas from a steel mill to ethanol and acetate, and Reaction 2 is the conversion of acetate by-product from Reaction 1 to $H_2$ and $CO_2$ gases. Gas produced by Reaction 2 is then introduced back into Reaction 1. Ethanol is recovered as the desired end-product of the process.

The process of the invention has particular applicability to the production of ethanol from gaseous substrates in which the level of hydrogen is relatively low, such as automobile exhaust gases and high volume CO-containing industrial flue gases. Examples include gases produced during ferrous metal products manufacturing, non-ferrous products manufacturing, petroleum refining processes, gasification of coal, gasification of biomass, electric power production, carbon black production, ammonia production, methanol production and coke manufacturing.

The invention enables such gaseous substrates to be used to produce ethanol by anaerobic fermentation, without the need to obtain hydrogen from another source. Also, because acetate produced as a by-product of the fermentation is converted into $H_2$ and $CO_2$ and returned to the fermentation process for use as a substrate for further ethanol production, the invention avoids the need to develop solutions for disposal of the acetate.

Reaction Stoichiometry

Without wishing to be bound by any theory, the applicants believe that the process of the present invention enables the fermentation reaction to take advantage of more efficient conversion stoichiometry of carbon to ethanol that occurs when sufficient $H_2$ is available. The reaction stoichiometry is described in more detail below.

Anaerobic bacteria have been demonstrated to produce ethanol and acetic acid from CO, $CO_2$ and $H_2$ via the acetyl CoA biochemical pathway. The stoichiometry for the formation of ethanol from CO and water is described in equation 1:

$$6CO + 3H_2O \Rightarrow CH_3CH_2OH + 4CO_2 \quad\quad 1.$$

The stoichiometry for the formation of acetic acid from CO is described in equation 2:

$$4CO + 2H_2O \Rightarrow CH_3COOH + 2CO_2 \quad\quad 2.$$

Thus, theoretically, with CO as the sole substrate carbon source, one third of the carbon from CO can be converted to ethanol, with the remaining two thirds being released as $CO_2$. However, according to the acetyl-CoA biochemical pathway, while the production of acetic acid is balanced in terms of the synthesis and consumption of adenosine triphosphate (ATP), the cell's energy currency, the production of ethanol results in a net consumption of ATP molecules. Therefore, the production of ethanol alone would not support energy intensive activities such as organism growth.

However, the availability of $H_2$ to micro-organisms known to catalyse the fermentation of CO to ethanol has been demonstrated to increase the ratio of ethanol to acetic acid production from CO, and the efficiency with which ethanol can be produced from CO. For example, WO 02/084348 contains data showing that elevated $H_2$ concentrations, of between 15 to 77% in the input gas substrate were a consistent feature of conditions described for ensuring increasing ethanol productivity in a gas-to-ethanol fermentation system.

Theoretically, in a fermentation substrate gas containing CO, $H_2$ and $CO_2$ at a concentration ratio of 1:1:0.33, two thirds of the CO can be converted to ethanol according to equations 3 and 4 below:

$$6CO + 3H_2O \Rightarrow CH_3CH_2OH + 4CO_2 \quad\quad 3.$$

$$6H_2 + 2CO_2 \Rightarrow CH_3CH_2OH + 3H_2O \quad\quad 4.$$

In combination these equations give the equation below:

$$6H_2 + 6CO \Rightarrow CH_3CH_2OH + 2CO_2 \quad\quad 5.$$

As described above, the ethanol production process of the present invention involves anaerobic fermentation of CO to ethanol and acetate in a bioreactor. The acetate by-product of the ethanol synthesis is converted into gaseous $H_2$ and $CO_2$. The resulting $H_2$ and/or $CO_2$ are returned to the fermentation for use as substrates.

Fermentation of CO to Alcohols and Acetate

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium lijungdahlii*, including those described in WO 00/68407, EP 117309, U.S. Pat. Nos. 5,173,429, 5,593,886, and 6,368,819, WO 98/00558 and WO 02/08438, and *Clostridium autoethanogenum* (Aribini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). The disclosures of each of these publications are fully incorporated herein by reference. In addition, other acetogenic anaerobic bacteria may be selected for use in the process of the invention by a person of skill in the art. It will also be appreciated that a mixed culture of two or more bacteria may be used in the process of the present invention.

One preferred micro-organism suitable for use in the present invention is *Clostridium autoethanogenum* that is available commercially from DSMZ and having the identifying characteristics of DSMZ deposit number DSMZ 10061.

The fermentation may be carried out in any suitable bioreactor, such as a continuous stirred tank reactor (CTSR), a bubble column reactor (BCR) or a trickle bed reactor (TBR). Also, in some preferred embodiments of the invention, the bioreactor may comprise a first, growth reactor in which the micro-organisms are cultured, and a second, fermentation reactor, to which fermentation broth from the growth reactor is fed and in which most of the fermentation product (ethanol and acetate) is produced.

As described above, the carbon source for the fermentation reaction is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

It will be appreciated that the processes of the present invention as described herein can be used to reduce the total atmospheric carbon emissions from industrial processes, by capturing CO-containing gases produced as a result of such processes and using them as substrates for the fermentation processes described herein.

Alternatively, in other embodiments of the invention, the CO-containing gaseous substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

It is generally preferred that the CO-containing gaseous substrate contains a major proportion of CO, and more preferably at least about 70% to about 90% CO by volume. It is not necessary for the gaseous substrate to contain any hydrogen. The gaseous substrate also preferably contains some $CO_2$, such as about 1% to about 30% by volume, such as about 5% to about 10% $CO_2$.

It will be appreciated that for growth of the bacteria and CO-to-ethanol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438 referred to above.

The fermentation should desirably be carried out under appropriate conditions for the CO-to-ethanol fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

The optimum reaction conditions will depend partly on the particular micro-organism used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, since a given CO-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, ie bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

Ethanol and Acetate Recovery

In preferred embodiments, a fermentation process according to the present invention described above will result in a fermentation broth comprising one or more alcohols, preferably ethanol, and acetate, as well as bacterial cells, in the liquid nutrient medium.

Ethanol is the preferred desired end product of the fermentation. The ethanol may be recovered from the fermentation broth by methods known in the art, such as fractional distillation or evaporation, and extractive fermentation.

Distillation of ethanol from a fermentation broth yields an azeotropic mixture of ethanol and water (ie 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetate may also be recovered from the fermentation broth using methods known in the art.

For example, an adsorption system involving an activated charcoal filter may be used. In this embodiment of the invention, it is preferred that microbial cells are first removed from the fermentation broth using a suitable separation unit. Numerous filtration-based methods of generating a cell free fermentation broth for product recovery are known in the art. The cell free ethanol—and acetate—containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used in the processes of the present invention. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

In certain preferred embodiments of the invention, ethanol and acetate are recovered from the fermentation broth by continuously removing a portion of the broth from the fermentation bioreactor, separating microbial cells from the broth (conveniently by filtration), and recovering first ethanol and then acetate from the broth. The ethanol may conveniently be recovered by distillation, and the acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Production of $H_2$ and $CO_2$ from Acetate

As outlined above, the process of the present invention involves recycling of the acetate by-product of the CO-to-ethanol fermentation, by converting it to $H_2$ and $CO_2$ gases and using the $H_2$ and/or $CO_2$ produced as a co-substrate for the fermentation micro-organisms to increase the efficiency of ethanol production.

Acetate may be converted to $H_2$ and $CO_2$ using methods known in the art.

For example, the conversion may be carried out chemically, such as by pyrolysis, that is, the chemical decomposition of organic materials by heating in the absence of oxygen or any other reagents.

However, it is generally preferred that the acetate conversion be carried out by microbial oxidation. Bacteria that are capable of catalysing the oxidation of acetate to $H_2$ and $CO_2$ are known in the art. Such bacteria include strains of the genus *Geobacter* that are capable of reducing Fe(III) to Fe(II), such as *Geobacter sulfurreducens*, and strains of the genus *Clostridium* such as *Clostridium ultunense*. One example of a strain of *Geobacter sulfurreducens* suitable for use in the present invention that has been demonstrated to oxidise acetate with the resultant production of $CO_2$ and $H_2$ is strain PCA, having the identifying characteristics of American Type Culture Collection (ATCC) Number 51573.

The microbial oxidation of acetate may be carried out in the same bioreactor in which the CO-to-alcohol fermentation is carried out. However, it is generally preferred that the microbial oxidation of acetate is carried out in a separate, second, bioreactor. In these embodiments, acetate is removed from the first bioreactor and introduced into the second bioreactor for conversion into $H_2$ and $CO_2$.

Nutrient media suitable for a process of microbial oxidation of acetate to $CO_2$ and $H_2$ in which acetate is the principal carbon and energy source are known in the art, and can be used in the processes of the present invention. For example, suitable media are described in publications of D R Lovley et al (Applied and Environmental Microbiology, 60, pp 3752-3759 (1994) and Applied and Environmental Microbiology 64, pp 2232-2236 (1998)). The media preparation desirably includes one or more electron acceptors, such as fumarate, Fe(III) ion, sulphate or nitrate. Alternatively, the electron acceptor may simply take the form of a graphite electrode. It is also preferred that the concentration of electron acceptor in the media preparation is limiting, as limiting the concentration of electron acceptors has been demonstrated to enhance the yield of $CO_2$ and $H_2$ from bioconversion by *Geobacter sulfurreducens* (D R Lovley et al, above). For example, a concentration of the electron acceptor of approximately 20 mM or less may be a limiting concentration. Once the level of the electron acceptor has been depleted, the microbial population must use an alternative strategy to dispose of electrons, in this case through the production of hydrogen.

Again, as for the CO-to-ethanol fermentation, the optimum process conditions for the culture system for conversion of acetate to $CO_2$ and $H_2$ will depend on the particular microorganism used. However, it is generally preferred that the level of evolved $H_2$ in the culture medium is maintained at a relatively low partial pressure, such as about 10 Pa or lower. This is to ensure that the reaction kinetics continue to favour the forward reaction for the production of $CO_2$ and $H_2$, rather than the reverse reaction (homoacetogenesis).

$H_2$ and/or $CO_2$ gas produced from the culture system is then introduced to the CO-to-ethanol fermentation being carried out in the first bioreactor, to increase the efficiency of the ethanol production process as described above. It is generally preferred that either $H_2$ or a mixture of $CO_2$ and $H_2$ is introduced into the first fermentation. $H_2$ may be separated from the resulting $CO_2/H_2$ gas mixture before introducing it to the CO-to-ethanol fermentation, using methods known in the art, or the $CO_2/H_2$ gas mixture may be introduced directly to the fermentation.

In certain embodiments of the invention, some of the $H_2$ produced by the conversion of acetate may be recovered separately for use as a source of hydrogen for another purpose, rather than being introduced into the CO-to-ethanol fermentation process.

FIG. 1 illustrates in schematic form a process of producing ethanol of the present invention. The process illustrated is a continuous process, which includes continuous nutrient feed, substrate gas feed, cell production in the bioreactor, cell removal from the bioreactor, and product removal. A continuous process results in a steady state being achieved in the bioreactor, in which the measurable variables, including feed rates, concentrations of substrate and nutrients, cell concentration in the bioreactor and rates of cell and product removal from the bioreactor, are within an optimal range over time.

Figure 2:
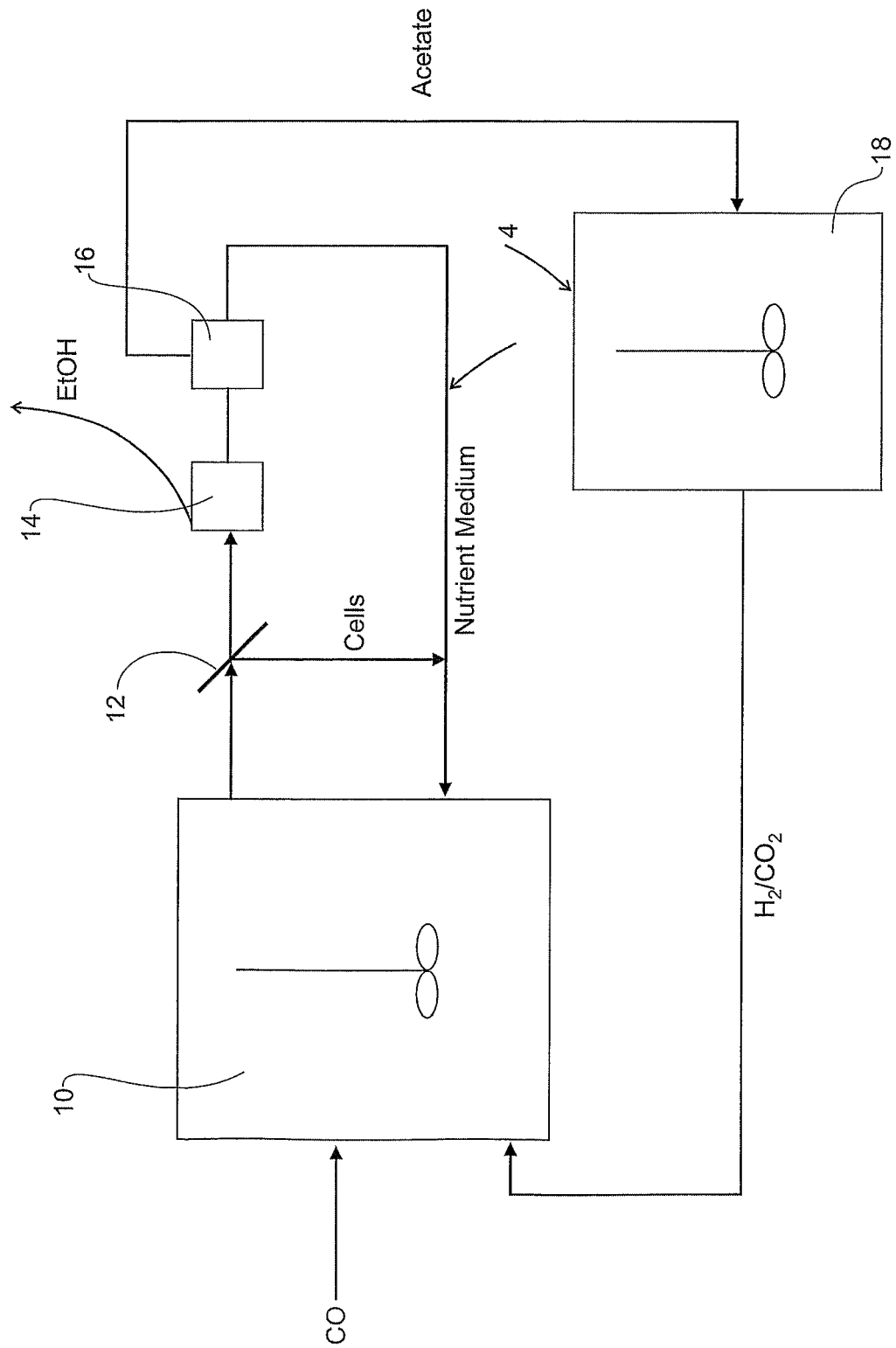
FIG. 2 is a schematic diagram of a process in accordance with an exemplary embodiment of the present invention.

Referring to FIG. 2, a CO-containing substrate gas and liquid nutrient medium 2 are fed continuously into a first bioreactor 10 containing culture of a bacterium such as *Clostridium autoethanogenum* that ferments CO to ethanol and acetate. A portion of the fermentation broth 6, containing the fermentation products acetate and ethanol, is continuously removed from the first bioreactor. The broth is fed to a filtration unit 12 that removes bacterial cells. The bacterial cells are returned to the bioreactor 10. Ethanol is removed from the resulting cell free permeate, conveniently by distillation, at processing station 14. Acetate is then removed from the ethanol-depleted cell free permeate, conveniently using activated charcoal, at processing station 16. The acetate and a liquid nutrient medium 4 are fed continuously to a second bioreactor 18, containing a culture of a bacterium such as *Geobacter sulfurreducens* that converts acetate to $CO_2$ and $H_2$. $H_2$ and $CO_2$ produced are continuously removed from the second bioreactor 18 and introduced into bioreactor 10.

Reaction Stoichiometry

Without wishing to be bound by any theory, the chemical reactions for the major steps of the ethanol-production process of the present invention are believed to be as follows:

1. The fermentation of CO to ethanol (a) and acetic acid (b):

$$18CO + 9H_2O \Longrightarrow 3CH_3CH_2OH + 12CO_2 \quad (a)$$

$$12CO + 6H_2O \Longrightarrow 3CH_3COOH + 6CO_2 \quad (b)$$

2. The breakdown of recovered acetic acid to hydrogen and carbon dioxide:

$$3CH_3COOH + 6H_2O \Longrightarrow 6CO_2 + 12H_2$$

3. Fermentation of the hydrogen and carbon dioxide breakdown products to ethanol:

Thus, the overall chemistry for the process is as follows:

wherein one third of all CO metabolized by the organism is captured as ethanol.

Fermentation of High CO Content Gaseous Substrates

In another aspect of the invention, the applicants have found that it is possible to ferment gaseous substrates having a higher CO content than that of gaseous substrates described in the prior art. Accordingly, in a further aspect, the present invention relates to a process of producing ethanol, the process comprising anaerobically fermenting a gaseous substrate comprising at least 70% CO by volume, such as about 75% to about 95% CO, using one or more strains of anaerobic acetogenic bacteria. It is generally preferred that the bacteria are from the genus Clostridia, as described above. In one preferred embodiment, the bacterium is Clostridium autoethanogenum, also as described above.

The invention will now be described in more detail with reference to the following non-limiting examples.

EXAMPLES

Introduction to Experimentation for Examples 1 to 5

Experimental aim: The aim of the following set of experiments was to demonstrate that acetate, a co-product formed during microbial gas-to-ethanol production with gas mixtures lacking hydrogen, could be used in a second microbial system to produce hydrogen gas, which, when recycled to a gas-to-ethanol production unit, resulted in improved gas-to-ethanol performance.

Review of method: The research goal was to demonstrate that the acetate co-product could be used as a resource of hydrogen production by G. sulfurreducens; and the hydrogen could be used to improve the gas-to-ethanol reaction with C. autoethanogenum growing on otherwise hydrogen-free gas mixtures. Headspace gas collected from cultures of G. sulfurreducens grown in serum bottles was pumped into the headspace of reaction vessels containing C. autoethanogenum and the effect on ethanol production determined.

Review of results: Effects of headspace gases from G. sulfurreducens grown with acetate as electron donor on the growth and productivity of C. autoethanogenum were monitored by measuring impacts on levels of acetate and ethanol production, growth rate of C. autoethanogenum, ratios of bacterial cells in the growth phase versus solventogenesis phase, and the effects on pH of the culture media.

Methods

Growth of G. sulfurreducens involved methods familiar to those experienced in the art of using this bacterial species (Caccavo, Lonergan et al. Appl. Environ. Microbiol 60(10); pp 3752-3759 (1994) and Cord-Ruwisch, Lovley et al., Appl. Envir. Microbiol 64(6): pp 2232-2236 (1998)). Cultures were grown and maintained on basal media (details below) for 5 days, using either 100% nitrogen or a mixture of 80% nitrogen and 20% $CO_2$ as headspace gases. These gas mixtures were also applied to the growth of G. sulfurreducens in a partial vacuum.

Cells were harvested by centrifugation and suspended in media containing 20 mM sodium acetate as electron donor, and 20 mM sodium fumarate as an electron acceptor. On depletion of the electron acceptor, fumarate, hydrogen gas ($H_2$) was formed as an alternative means of electron removal through donation of electrons to protons. The energetics of this pathway became limiting at low partial pressures of hydrogen, (50 Pa), at which the reaction becomes unfavorable (Cord-Ruwisch, Lovley et al. 1998, above and Esteve-Núñez, Rothermich et al. 2005 Environ. Microbiol. 7(5): 641-648 (2005)). At the point that the hydrogen partial pressure became maximal the gas was displaced with culture media and collected. The use of strong >5 M potassium hydroxide (carbosorb) to sequester carbon dioxide and hence increase the hydrogen partial pressure enabled the concentration of the hydrogen. Gas was harvested at the peak of hydrogen production, after which the culture was grown for at least 2 more days and gas harvested again. Cells were maintained in 240 ml serum bottles in 50 mL of media with 190 ml headspace. Serum bottles were gas tight with all additions of media, gases and culture through the use of syringes and needles. Bottles were agitated at 150 rpm in a 35 degree Celsius incubator.

Base Media Used to Grow G. sulfurreducens

| Media Component | Concentration per 1.0 L of Media |
|---|---|
| $NH_4Cl$ | 0.25 g |
| $NaH_2PO_4$ | 0.60 g |
| KCl | 0.10 g |
| $NaHCO_3$ | 2.50 g |
| Wolfe's vitamin solution (LS01) | 10 mL |
| Composite mineral solution (LS06) | 10 mL |
| Electron Donor | |
| 20 mM Acetate (sodium acetate trihydrate) | 2.7216 g |
| Electron Acceptor | |
| 20 mM Sodium fumarate | 3.208 g |
| Cysteine•HCL (5 mM) | 0.878 g |
| Resazurin | 0.5 mL |
| Deionised $H_2O$ | To 1 L |
| Original gas dispensed under | 100% Nitrogen or 80% N2 20% CO2 |

| Method - |
|---|
| 1. Gas out this media with gas mixture 80% Nitrogen and 20% Carbon Dioxide (or pure $CO_2$ until pH drops to 6.8) over heat while stirring with a long cannula blowing near the surface of the media. Media changes colour from blue to pink. |
| 2. Once the media approaches boiling point, add cysteine. Media should change colour from pink to clear. |
| 3. Pipette into gassed out tubes. Cap, crimp, and autoclave. |
| 4. Dispense under nitrogen and adjust CO2 content after autoclaving |
| 5. Optimum growth temperature for Geobacter sulfurreducens is 35° C. at pH 6.8. |

Headspace Vacuum

Growth of G. sulfurreducens was carried out under a modified headspace atmosphere. Growth was initiated under a 100% carbon dioxide atmosphere, which was evacuated to at least −25 inches mercury Hg (gauge), leaving a $CO_2$ partial pressure of 16.6 kilo Pascals (kPa). The growth under such an atmosphere allowed for maximum hydrogen production. As $CO_2$ is easily absorbed by carbon dioxide scrubbing solutions, hydrogen can in effect be concentrated and collected for use in the subsequent reaction. The use of a vacuum to "scavenge" hydrogen and keep the reaction favourable is one example as to how this reaction could proceed continuously in a commercial operation.

Growth of C. autoethanogenum

Growth of C. autoethanogenum was based on the medium used by Phillips et al 1993 (Phillips, Klasson, Clausen and Gaddy, Applied Biochemistry and Biotechnology, 39/40 pp 559-571 (1993)). Various gas mixtures were used in the headspace, including 100% nitrogen, 100% $CO_2$, 95% CO plus 5% $CO_2$, 50% CO, 35% nitrogen, 10% $CO_2$ plus 5% hydrogen. For growth, media pH was initially adjusted to pH 6.0, whereas for ethanol production, media pH was reduced to pH 4.5.

During growth and solventogenesis, cells were maintained in 15 ml vials or 200 ml serum bottles under continuous agitation to increase gas-to-liquid mass transfer. For experiments with *Geobacter*-gas, cells were harvested and suspended in fresh media, with various gas mixtures in the headspace. For these latter experiments, cells were transferred to 1.5 ml gas tight reaction vials with screw caps and butyl rubber septa. The reaction vials were agitated continuously, and gas mixtures were replaced every five days.

Media Composition for *C. autoethanogenum*

| Media Component | Concentration per 1.0 L of Media |
| --- | --- |
| $MgCl_2 \cdot 6H_2O$ | 0.5 g |
| NaCl | 0.2 g |
| $CaCl_2$ | 0.2 g |
| $(NH_4)_2HPO_4$ | 2.0 g |
| 85% $H_3PO_4$ | 0.05 ml |
| KCL | 0.15 |
| Composite trace metal solution | 10 mL |
| Composite B vitamin Solution | 10 mL |
| Resazurin (1000 mg/L stock) | 1 mL |
| $FeCl_3$ | 0.0025 g |
| Cystine HCL | 0.75 g |
| Distilled Water | To 1 liter |

Wolfe's Vitamin Solution

| ** Wolfe's Vitamin Solution | per L of Stock |
| --- | --- |
| Biotin | 2.0 mg |
| Folic acid | 2.0 mg |
| Pyridoxine hydrochloride | 10.0 mg |
| Thiamine•HCl | 5.0 mg |
| Riboflavin | 5.0 mg |
| Nicotinic acid | 5.0 mg |
| Calcium D-(*)-pantothenate | 5.0 mg |
| Vitamin B12 | 0.1 mg |
| p-Aminobenzoic acid | 5.0 mg |
| Thioctic acid | 5.0 mg |
| Distilled water | To 1 Liter |

Composite Mineral Solution

| Composite Mineral Stock Solution | Composite trace mineral stock solution |
| --- | --- |
| Nitrilotriacetic acid | 1.5 g |
| $MgSO_4 \cdot 7H_2O$ | 3.0 g |
| $MnSO_4 \cdot H_2O$ | 0.5 g |

-continued

| Composite Mineral Stock Solution | Composite trace mineral stock solution |
| --- | --- |
| NaCl | 1.0 g |
| $MnCl_2 \cdot 4H_2O$ | |
| $FeSO_4 \cdot 7H_2O$ | 0.1 g |
| $Fe(SO_4)_2(NH_4)_2 \cdot 6H_2O$ | 0.8 g |
| $FeCl_2 \cdot 4H_2O$ | |
| $CoCl_2 \cdot 6H_2O$ | 0.2 g |
| $CaCl_2$ | |
| $ZnSO_4 \cdot 7H_2O$ | 0.2 g |
| $CuSO_4 \cdot 5H_2O$ | |
| $CuCl_2 \cdot 2H_2O$ | 0.02 g |
| $AlK(SO_4)_2 \cdot 12H_2O$ | 0.02 g |
| $H_3BO_3$ | 0.30 g |
| $NaMoO_4 \cdot 2H_2O$ | 0.03 g |
| *$Na_2SeO_3$ | 0.02 g |
| *$NiCl_2 \cdot 6H_2O$ | 0.02 g |
| *$Na_2WO_4 \cdot 6H_2O$ | 0.02 g |
| Distilled Water | To 1 Liter |

Acetate and Ethanol Determinations

Apparatus

Ethanol and Acetate determinations were made using a gas chromatograph HP 5890 series II—Utilizing a flame ionization detector (FID), removable, deactivated glass, injection port liner, associated regulators, gas lines, and septa with sample autoinjector HP 7673A. Separations were made on a capillary GC Column EC1000—Alltech EC1000 30 m×0.25 mm×0.25 μm.

The Gas Chromatograph was operated in Split mode with a total flow of hydrogen of 50 mL/min with 5 mL purge flow (1:10 split), a column head pressure of 10 psig resulting in a linear velocity of 45 cm/sec. The temperature program was initiated at 60° C., hold for 1 minute then ramped to 170° C. at 30° C. per minute, then held for 3 minutes. This resulted in a total run time of 8 minutes. Injector temperature was 180° C. and the detector temperature was 225° C.

Reagents used were Propan-1-ol-Reagent grade. Scharlau AL0437, Min assay by GC 99.5%;

Ethanol absolute—Scharlau ET0015, Min assay by GC 99.9; Acetic acid 100% glacial—BDH 100015N, Min assay by GC 99.8%; Orthophosphoric acid-BDH 294214Q, Min assay by GC 99.0%; Nitrogen—BOC Oxygen Free-GC make up gas; Hydrogen—BOC Oxygen Free-GC carrier gas and FID fuel; Zero air-FID oxidant; Water-deionized.

Collection of Head-Space Gases

Gas samples from the headspace of the serum bottles containing *G. sulfurreducens* were collected by displacement with fresh media though a 10M KOH solution to remove excess $CO_2$ gas used in the culture headspace of *G. sulfurreducens*.

Example 1

Adaptation and Growth of *Clostridium autoethanogenum* with Zero Hydrogen Gas Mixes Aim: to determine the impact on the growth of *C. autoethanogenum* of 5 ml of hydrogen gas in a headspace of 10 ml of 95% CO, 5% $CO_2$ pressurized to 25 psig.

15 ml Hungate tubes containing 5 ml of bacterial culture in a defined medium were incubated at 37° C. with either with a headspace of 95% CO, 5% $CO_2$, or 1 ml $H_2$ gas in a 95% CO, 5% $CO_2$ gas mix. All tubes were pressurized to 25 psig with 95% CO, 5% $CO_2$ gas.

Bacterial growth was determined by measuring the optical density (OD) at 620 nm of the culture broth after 0, 2, 5 and 10 days using a DYNEX technologies, opsys MR plate reader.

Note: for day 10, data is only available for the growth of *C. autoethanogenum* in Hungate tubes with a headspace containing with 95% CO, 5% $CO_2$ Results In each case, data shown is the average of three replicates.

| Days | 95% CO, 5% $CO_2$ | std dev | 1 ml $H_2$ + 95% CO, 5% $CO_2$ + $H_2$ | std dev |
|---|---|---|---|---|
| 0 | 0.039 | 0.000 | 0.039 | 0.000 |
| 2 | 0.040 | 0.001 | 0.056 | 0.001 |
| 5 | 0.041 | 0.001 | 0.106 | 0.011 |
| 10 | 0.085 | 0.015 | | |

Figure 3:
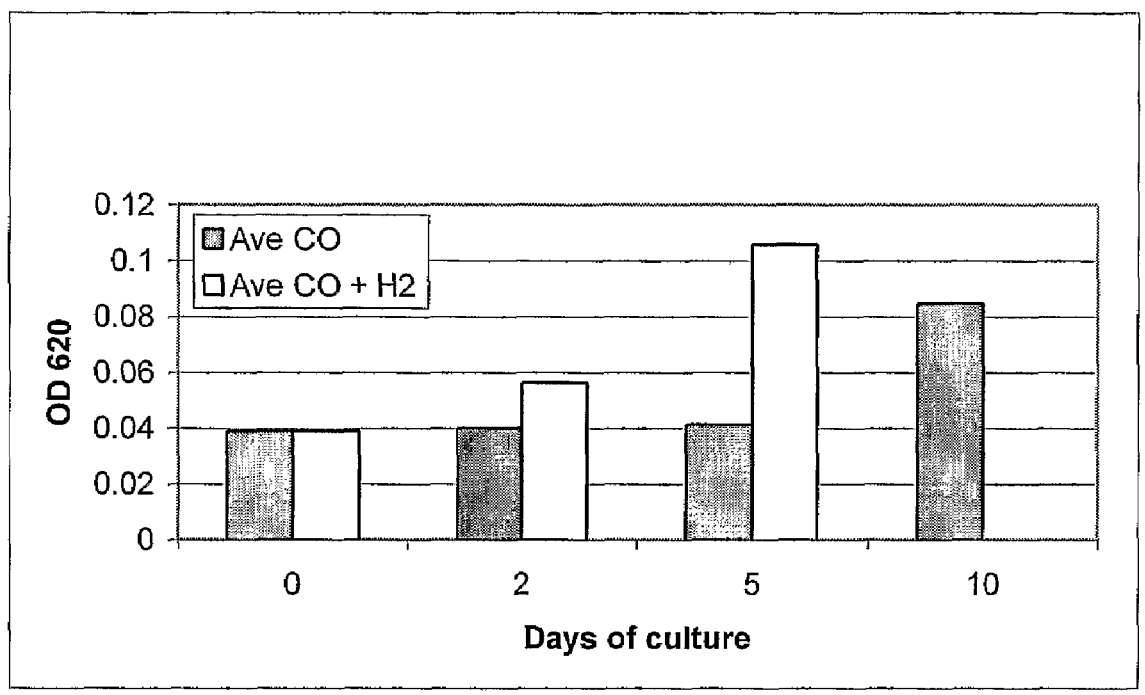
FIG. 3 is a graph showing the impact of hydrogen gas on the growth of *Clostridium autoethanogenum* on carbon monoxide.

Growth of *C. autoethanogenum* on a $CO/CO_2$ gas mix was measured in the presence and absence of $H_2$ gas. The results are shown graphically in FIG. 3 and indicate that under the conditions used, the addition of 1 ml of $H_2$ to a headspace of 10 ml pressurized to 25 psig with a 95% CO/5% $CO_2$ gas mix, increased the growth rate of the bacteria. Bacteria grown on the 95% CO/5% $CO_2$ gas mix alone reached an OD 620 of 0.085 after 10 days of incubation, while those grown in the presence of hydrogen reached an equivalent, or higher OD 620 after only 5 days of culture incubation.

Example 2

*Geobacter sulfurreducens* Grown on Acetate

Aim: to determine the kinetics of acetate degradation by *Geobacter sulfurreducens*

For this experiment, Hungate tubes with an internal volume of 30 ml were inoculated with 10 ml of a fresh water basal media containing 20 mM reagent grade acetic acid as the sole carbon source for bacterial growth. Tubes were autoclaved, after which, for each tube, the pH of the solution was adjusted to 6.5 and the Redox potential of the solution was adjusted to ~−85 mV. Tubes were inoculated with 0.1 ml of *G. sulfurreducens* and incubated at 35° C.

Acetate levels were measured using a Hewlett Packard 5890 (II) gas chromatograph.

Results:

All data points are the average of at least two replicates.

|  | Days | | | |
|---|---|---|---|---|
|  | 0 | 3 | 6 | 11 |
| Acetate (g/l) | 1.292 | 0.135 | 0.210 | 0.216 |
| Std Dev | 0.139 | 0.011 | 0.106 | 0.095 |

Figure 4:
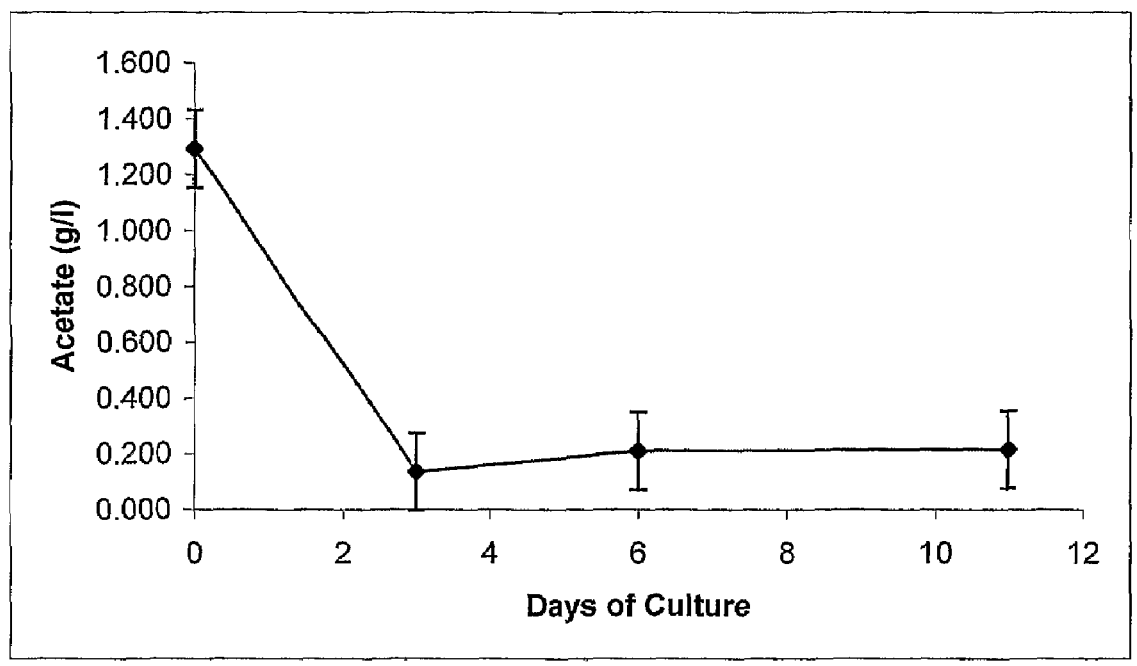
FIG. 4 is a graph showing the degradation of acetate with time by *Geobacter sulfurreducens*.

The results are shown graphically in FIG. 4 and describe the degradation of acetate with time by *G. sulfurreducens*. Under the conditions used, acetate degradation had ceased after three days of microbial culture. The rate of acetate degradation over the period from day 0 to day 3 was 0.3857 g/l/day.

Example 3

*Geobacter sulfurreducens* Hydrogen Production in Serum Bottles

Aim: to collect and measure biologically produced hydrogen gas resulting from the degradation of acetate by *G. sulfurreducens* from the headspace of these cultures, for use as a substrate in the gas to ethanol reaction.

Materials:
1. *G. sulfurreducens* subculture
2. LM12 acceptor limiting media with 20 mM acetate and 20 mM fumarate. Media is enclosed in 240 mL serum bottles stoppered with thick butyl rubber septum, under a headspace of food grade carbon dioxide evacuated to −25″ Hg.
3. Needles, syringes and isopropanol wipes.
4. Incubator at 35° C.
5. Shaking platform set at 50 RPM.
6. 4, 5 and 10 M KOH solution.
7. Oxygen free nitrogen
8. Food grade carbon dioxide.
9. ¼′ thick butyl rubber tubing.
10. 0.22 um syringe filters
11. Sterile 240 mL serum bottle under atmosphere of carbon dioxide
12. Luer-lok 2-way stopcocks (Bio-Rad)

Gas collected from *G. sulfurreducens* was cultured in serum bottles, by the method described below:

1. A syringe needle connected to the gassing manifold was inserted into a serum bottle containing *Geobacter* media, this is referred to as serum bottle 1.
2. A 15 cm butyl rubber tube with a 2-way stopcock at each end attached to a hypodermic needle, was used to connect serum bottle 1 to a second serum bottle containing *Geobacter* media. This is referred to as serum bottle 2.
3. Another 15 cm butyl rubber with a 2-way stopcock connecting the tube to a hypodermic needle at each end, was used to connect serum bottle 2 to a third serum bottle containing 10M KOH. This is referred to as serum bottle 3.
4. The needle inserted into serum bottle 3 had a hydrophobic filter to ensure no KOH could travel out of the serum bottle filled with KOH.
5. Serum bottle 3 containing the KOH was prepared by first autoclaving the serum bottle under an atmosphere of carbon dioxide. 50 mL of 10M KOH was then injected into the serum bottle, resulting in a strong vacuum within the serum bottle through the reaction of KOH with $CO_2$ ($2KOH+CO_2=K_2CO_3+H_2O$).
6. Once the three serum bottles were connected in series they formed a gradient from high pressure to low across each of their head spaces into the KOH solution in serum bottle 3, as all headspaces are expected to contain $CO_2$ plus small amounts of hydrogen.
7. The gas from each serum bottle was then progressively transferred into the KOH containing bottle by means of liquid displacement.
8. Firstly $CO_2$ gas was passed into serum bottle 1, increasing the pressure inside serum bottle 1.
9. Serum bottle 1 was then turned upside down so that the media inside the bottle covered the septum, and the carbon dioxide flow passed through this media.
10. Next the stopcocks connecting serum bottle 1 to serum bottle 2 were opened resulting in media being pushed from serum bottle 1 into serum bottle 2.
11. Next, serum bottle 3, was turned upside down so that any gas displaced out of serum bottle 2 by the media flowing into it from serum bottle 1, passed into serum bottle 3 through the KOH solution.
12. The stopcocks connecting serum bottle 2 to serum bottle 3 were opened.
13. Gas from serum bottle 2 was displaced into serum bottle 3 and the carbon dioxide present in the headspace absorbed by the KOH solution.
14. Serum bottle 2 now contained 100 mL of media
15. After all the media was removed from serum bottle 1, all connections were turned to the opp position and serum bottle 1 was removed from the sequence. Serum bottle 2 was transferred to the serum bottle 1 position, and another serum bottle containing *G. sulfurreducens* culture was placed in the serum bottle 2 position.
16. The process is repeated until one serum bottle contained 200% of media and was then used to displace the gas in all the remaining bottles.
17. Once the gas was harvested from all culture serum bottles, the collected gas in serum bottle 3 was brought to atmospheric pressure by displacing the vacuum inside this bottle with 10M KOH.

Figure 5:
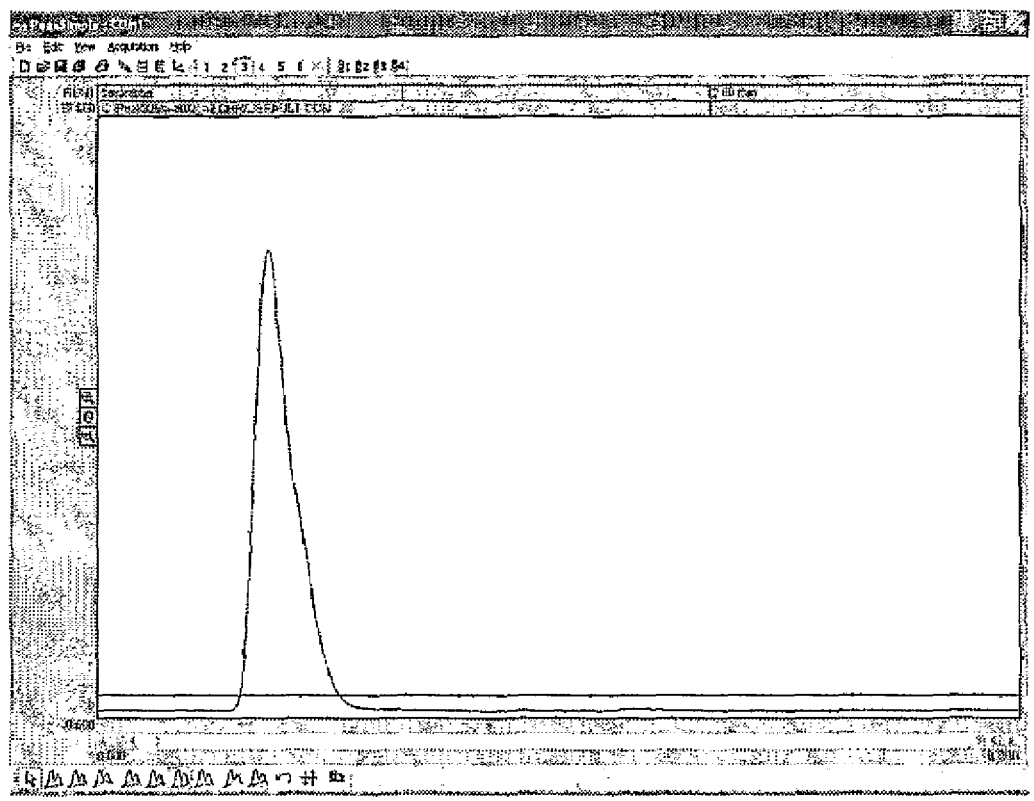
FIG. 5 is a gas chromatogram of gas produced by degradation of acetate by *Geobacter sulfurreducens*, from which $CO_2$ has been removed.

GC Set-Up for Hydrogen and Carbon Dioxide Detection
  a. Shimadzu GC-8A with TCD
  b. Nitrogen as a carrier gas
  c. Alltech 10.0% AT1000 80/100 CW/AW 6'×⅛ SS column
  d. 0.2 mL injection
  e. Oven temperature 60° C. isothermal
  f. Injector and detector temperatures 160° C.
Results:

The gas chromatogram of the $CO_2$ depleted gas is shown in FIG. 5. This shows a large $H_2$ peak. An $O_2$ peak may also be present as part of the $H_2$ peak (a slight shoulder visible on the right hand side of the $H_2$ peak pictured in FIG. 5).

Quantification of the amount of $H_2$ in the collected gas sample was not possible at this time, although researchers in the lab of Prof. Hicham Idris who observed this measurement, described this as a very significant concentration potentially constituting several percent of the sample gas.

Example 4

*Geobacter sulfurreducens* Grown on Biologically Produced Acetate from *Clostridium autoethanogenum* Cultures Aim: to determine if the bacterium *Geobacter sulfurreducens* is able to degrade acetate (acetic acid) produced from the growth of another bacterium *Clostridium autoethanogenum*. During the gas to ethanol process *Clostridium autoethanogenum* produces acetic acid as a by product of ethanol production. This experiment will take media in which *Clostridium autoethanogenum* has grown (referred to as conditioned media) and produced ethanol along with acetic acid and attempt to remove it through oxidation by *Geobacter sulfurreducens*.

For this experiment, Hungate tubes with an internal volume of 20 ml were inoculated with a 1 ml of a 10× stock of fresh water basal media and 9 ml of conditioned media. Tubes were autoclaved, after which, for each tube, the pH of the solution was adjusted ~7.0 and the Redox potential of the solution was adjusted to ~−115 mV. Tubes were inoculated with 0.1 ml of *G. sulfurreducens* and incubated at 35° C.

Ethanol and acetate levels in each culture were measured using a Hewlett Packard 5890 (II) Gas chromatograph.
Results:
All data points are the average of at least two replicates.

|  | Days | | | |
| --- | --- | --- | --- | --- |
|  | 0 | 3 | 6 | 11 |
| Ethanol (g/l) | 1.6965 | 1.6843 | 1.7188 | 1.82485 |
| Acetate (g/l) | 1.66305 | 0.29425 | 0.36135 | 0.3924 |

Figure 6:
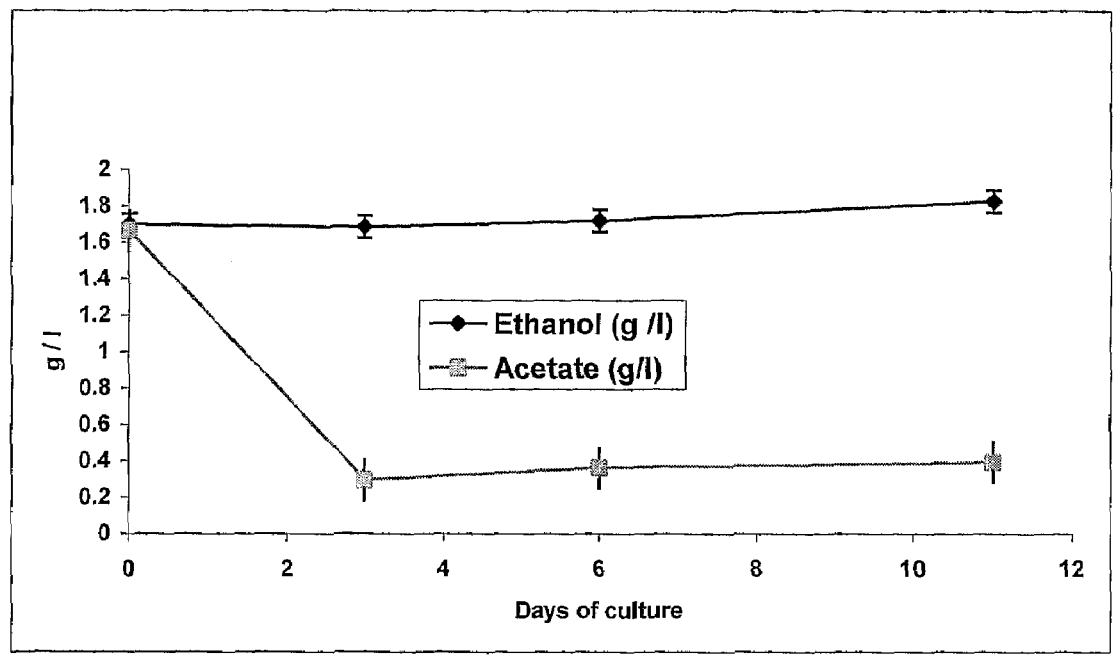
FIG. 6 is a graph showing the degradation by *Geobacter sulfurreducens* of acetate produced by *Clostridium autoethanogenum*.

The results are shown graphically in FIG. 6 and describe the degradation of acetate with time by *G. sulfurreducens* in conditioned media containing ethanol. Under the conditions used, acetate degradation had ceased after three days of incubation. The rate of acetate degradation over the period from day 0 to day 3 was 0.456 g/l/day. This rate of acetate degradation is almost identical to that recorded in a previous experiment in which the microbe was grown in fresh media containing 20 mM acetate. Therefore, acetate degradation was apparently not inhibited by the presence of ethanol, or other compounds potentially produced by the *C. autoethanogenum* culture.

Example 5

Impact of *G. sulfurreducens* Off-Gas on *C. autoethanogenum* Cultures

Aim: to determine the impact of enriched gas, collected from the headspace of cultures of *G. sulfurreducens* on ethanol and acetate production by *C. autoethanogenum*.

Established *C. autoethanogenum* cultures were incubated in the presence of the following gases at 37° C. for 7 days:

| Gas | Abbreviation |
| --- | --- |
| 95% CO/5% $CO_2$ + 1 ml of enriched headspace gas from cultures of *G. sulfurreducens* | $CO/CO_2$ + Gs-gas |
| 100% $CO_2$ + 1 ml of enriched headspace gas from cultures of *G. sulfurreducens* | $CO_2$ + Gs-gas |
| 95% CO/5% $CO_2$ | $CO/CO_2$ |
| 100% $N_2$ | $N_2$ |
| 100% $CO_2$ | $CO_2$ |

Ethanol and acetate production was measured using a Hewlett Packard 5890 (II) Gas chromatograph.
Results:
All data points are the average of at least two replicates.

| Gas | Ethanol (g/l) | Ethanol (std dev) | Acetic Acid (g/l) | Acetate (std dev) | E:A ratio |
| --- | --- | --- | --- | --- | --- |
| $CO/CO_2$ + Gs-gas | 0.0220 | 0.0010 | 0.0117 | 0.0035 | 1.8750 |
| $CO/CO_2$ | 0.0057 | 0.0021 | 0.0086 | 0.0026 | 0.6628 |
| $N_2$ | 0.0000 | 0.0000 | 0.0000 | 0.0000 |  |
| $CO_2$ | 0.0000 | 0.0000 | 0.0000 | 0.0000 |  |

Figure 7:
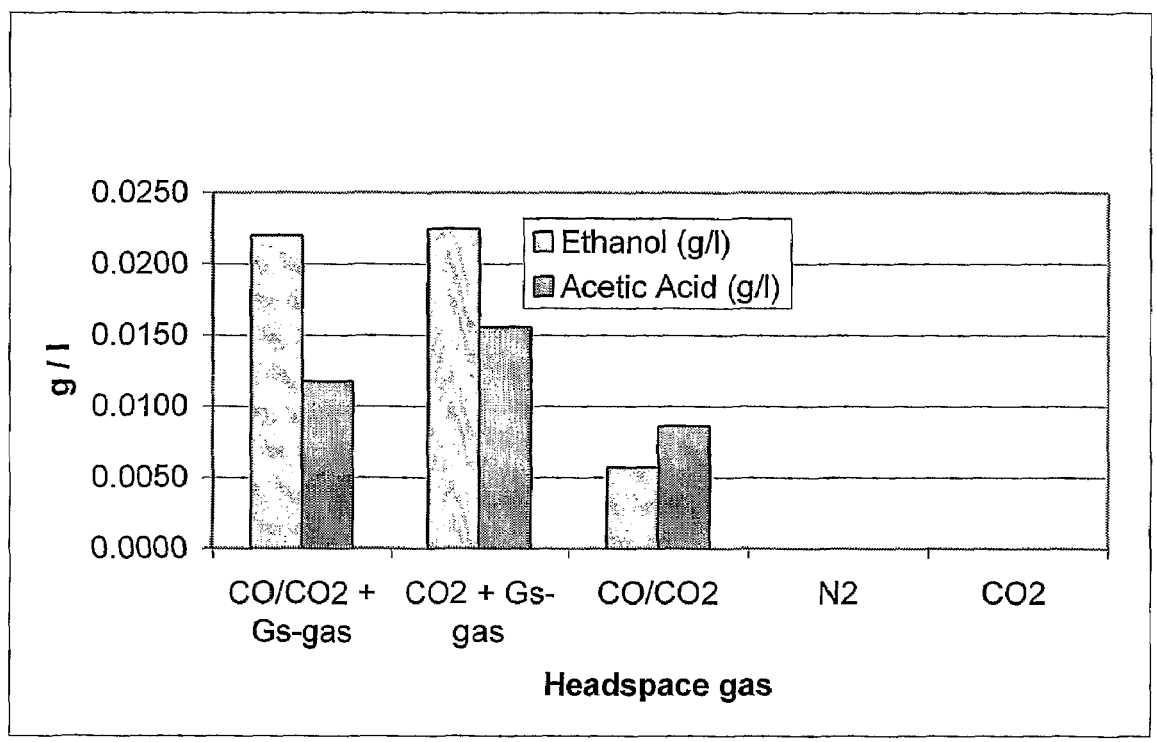
FIG. 7 is a graph showing the impact of gas collected from the headspace of cultures of *Geobacter sulfurreducens* on ethanol and acetate production by *Clostridium autoethanogenum*.

The results are shown graphically in FIG. 7 and contrast the production of ethanol and acetate by cultures incubated with a headspace of either $CO/CO_2$ or $CO_2$, with those incubated with these same gases plus Gs-gas under the conditions used. When introduced into a headspace of $CO/CO_2$, Gs-gas had the impact of both increasing the overall levels of acetate and ethanol produced by the culture, and reversing the ratio of products formed in favour of ethanol. When Gs-gas was introduced into a headspace of $CO_2$ it had the impact of enabling the culture to produce ethanol and acetate. No ethanol or acetate was produced by control cultures incubated with a headspace of $CO_2$ alone or N2 alone.

Example 6

Impact of *G. sulfurreducens* Off-Gas on Growth of *C. autoethanogenum* Cultures Experimental Procedure
Reaction 1: Growth of *C. autoethanogenum*

*C. autoethanogenum* was grown under anaerobic conditions in 1.6 litres of fermentation media in a 2.25 litre New Brunswick Scientific Bioflo 2000 Fermenter apparatus at 37° C. A typical media composition is described in table 1, table 2 and table 3 (below). Throughout the fermentation the input gas flow rate was maintained at 4 ml/min through a calibrated rotameter apparatus at atmospheric pressure. The input gas was switched between the standard fermentation gas mix (standard fermentation gas composition was 95% CO, 5% $CO_2$) and the exit gas from a *G. sulfurreducens* fermentation using acetate recovered from the *C. autoethanogenum* culture as the electron donor and sole source of carbon. To facilitate gas-liquid mass transfer the reaction media was continuously stirred at 400 rpm. Media pH was monitored using a pH Ferm probe (Broadly James Corp.) and the media Redox potential was monitored using a Redox Ferm probe (Broadly James Corp.). The output from each probe was read via a Jenco 6309POT (Jenco Instruments). A feedback control loop was established between the Jenco control unit and peristaltic dosing pumps (Wheaton Science Products) linked separately to acid and base buffers. Throughout the course of this experiment the fermenter media was maintained at a pH of between 5.5 and 5.8 through the automated addition of 5M sodium hydroxide. The fermentation media was routinely sampled in an aseptic and anaerobic manner in order to allow a determination of ethanol, acetate and cell biomass accumulation with time.

Recovery of Acetic Acid

Accumulated acetate concentrations in the *C. autoethanogenum* culture media were maintained within a range from 5 g/l and 30 g/l throughout the culture period. To achieve this, cell-free culture media was removed from the reaction vessel via a cross-flow membrane filter (Vivaflow 200, 100,000 MWCO, PES, VivaScience). A 1.6 liter working volume was maintained in the fermentation vessel through the addition of fresh anaerobic, autoclaved media. Addition of the fresh media to the fermentation vessel was conducted under an atmosphere of 95% CO, 5% $CO_2$.

Reaction 2: Growth of *G. sulfurreducens*

*G. sulfurreducens* was grown under anaerobic conditions in 1.6 liters of fermentation media in a 2.25 liter New Brunswick Scientific Bioflo 2000 Fermenter apparatus at 35° C. *G. sulfurreducens* culture media was formulated using the acetate containing media recovered by cross-flow membrane filtration from the *C. autoethanogenum* culture. A typical media composition is described in table 4 and table (below) and includes the use of a limiting concentration (20 mM) of the electron acceptor sodium fumarate. The final concentration of acetate in the media was adjusted to between 2 and 5 g/l. Throughout the fermentation the input gas flow rate was maintained at 4 ml/min through a calibrated rotameter apparatus at atmospheric pressure. The input gas composition was 95% CO, 5% $CO_2$. The exit gas from the fermenter was either vented to the atmosphere or passed through a 0.25 μm filter and used as the input gas for the *C. autoethanogenum* containing fermenter (reaction 1 described above). The reaction media was continuously stirred at 50 rpm. Media pH was monitored using a pH Ferm probe (Broadly James Corp.). The output from each probe was read via a Jenco 6309POT Genco Instruments). The fermenter media was inoculated with bacteria from a number of 50 ml *G. sulfurreducens* cultures grown in the media described below (see tables 4 & 5 below), ie electron acceptor limiting media with 20 mM acetate and 20 mM fumarate. Media was enclosed in 240 mL serum bottles sealed with thick butyl rubber septa under a headspace of 80% $N_2$, 20% $CO_2$ gas mix at 10 psig. The initial pH of the fermentation media was 6.8. The fermentation media was routinely sampled in an aseptic and anaerobic manner in order to allow a determination the of acetate concentration with time.

Linkage of *G. sulfurreducens* and *C. autoethanogenum* fermentations

Fermentations of *G. sulfurreducens* using acetate recovered from the fermentation of *C. autoethanogenum* were performed in the presence of a continuous stream of 95% CO 5% $CO_2$ gas at a flow rate of 4 ml/min. Under electron-acceptor limiting conditions, the oxidation of acetate by *G. sulfurreducens* results in the production of $CO_2$ and $H_2$. Under these conditions, the exit gas stream from this fermentation is anticipated to contain CO, $CO_2$ and $H_2$. After an initial period of bacterial growth, the exit gas stream from the *G. sulfurreducens* culture was channelled via a ⅛ inch stainless steel tubing through the input gas sparger of the *C. autoethanogenum* fermenter to replace the original 95% CO, 5% $CO_2$ input gas at the same gas flow-rate. Care was taken throughout the linkage process to ensure that anaerobicity of both fermentations was maintained. Linkage experiments were undertaken and monitored for either 24 or 48 hour periods. The impact of fermenter linkage on bacterial growth and acetate production in the *C. autoethanogenum* fermentation were determined by comparison with observations made under control (non-linked) conditions.

Figure 8:
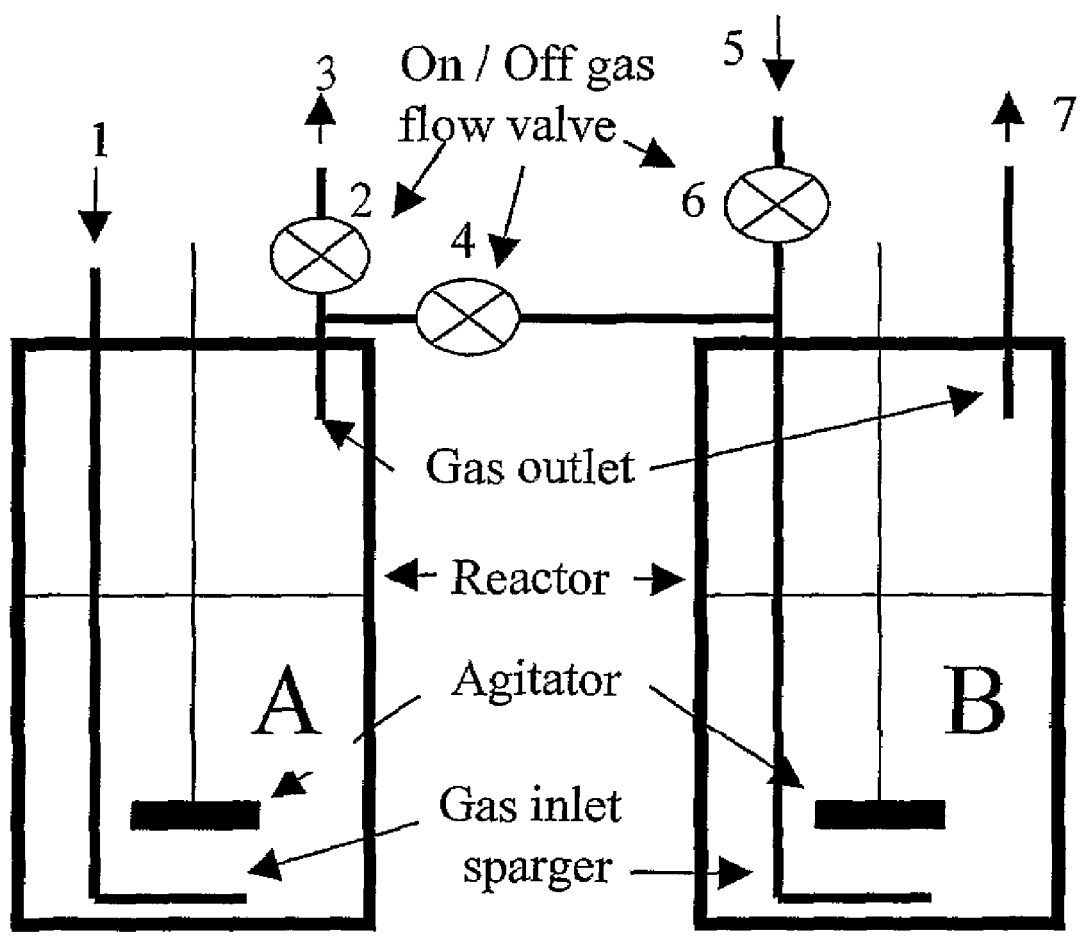
FIGS. 8 and 9 are schematic diagrams illustrating processes of the present invention as described in Examples 6 and 7, respectively.

The reactor setup is shown in FIG. 8 and described below.

*Geobacter sulfurreducens* and *Clostridium autoethanogenum* were separately cultured in defined culture media in reactors A and B respectively. Initially, a gas stream consisting of 95% CO and 5% $CO_2$ was introduced into each reactor separately via gas inlet spargers 1 and 5 respectively. At this time valve 2 was open, valve 4 was closed and valve 6 was open. The gas flow rate from gas outlet 7 was recorded.

In order to determine the impact of off-gases generated in reactor A on the performance of the culture in reactor B the following actions were taken in sequence:
1. Gas flow valve 2 was closed
2. Gas flow valve 4 was opened
3. Gas flow valve 6 was closed
4. The gas flow rate from gas outlet 7 was measured and the gas inlet flow rate into reactor A through gas inlet sparger 1 was adjusted to ensure that the gas flow rate through reactor B remained constant.

Determination of Ethanol, Acetic Acid and Bacterial Cell Density

Ethanol and acetate determinations were made using the method described for Examples 1 to 5 above. Bacterial growth was determined by measuring the optical density (OD) at 620 nm of the culture broth after 0, 2, 5 and 10 days using a DYNEX technologies, opsys MR plate reader. These data were translated into bacterial dry mass.

Results

The impact of exit gases from a *G. sulfurreducens* fermentation oxidising acetate under electron donor limited conditions on bacterial growth by a *C. autoethanogenum* fermentation was determined. Three linkage example experiments were carried out, each representing increasing rates of acetate degradation by the *G. sulfurreducens* culture.

Experiment 1

A *G. sulfurreducens* fermentation was initiated in 1.6 litres of media with three pooled 50 ml *G. sulfurreducens* cultures grown in media described in table 4, and table 5 (below). After an initial period of bacterial growth, exit gas from the *G. sulfurreducens* fermentation was linked to the inlet gas sparger of an established *C. autoethanogenum* fermentation. Media samples were taken from the *C. autoethanogenum* culture every 24 hours for a 48-hour period prior to the linkage of this culture with the *G. sulfurreducens* culture. Analysis of these samples revealed that the culture was accumulating bacterial cell biomass at a rate of 13.9 mg dry mass/liter of fermentation media per day. Upon linking the two fermenter systems, media samples were taken from the both the *C. autoethanogenum* fermenter and the *G. sulfurreducens* media every 24 hours for a 48-hour period culture. Analysis of these samples revealed that the rate of *C. autoethanogenum* bacterial cell biomass accumulation had increased to 17.4 mg dry mass/liter of fermentation media per day, a difference of 3.5 mg dry mass/liter of fermentation media per day. During this period the *G. sulfurreducens* culture degraded acetate at a rate of 0.8 g of acetate per litre per day.

Experiment 2

A *G. sulfurreducens* fermentation was initiated in 1.6 litres of media with four pooled 50 ml *G. sulfurreducens* cultures grown in media described in table 4, and table 5 (below). After an initial period of bacterial growth, exit gas from the *G. sulfurreducens* fermentation was linked to the inlet gas sparger of an established *C. autoethanogenum* fermentation. Media samples were taken from the *C. autoethanogenum* over a 24-hour period prior to the linkage of this culture with the *G. sulfurreducens* culture. Analysis of these samples revealed that the culture was accumulating bacterial cell biomass at a rate of 9.8 mg dry mass/liter of fermentation media per day. Upon linking the two fermenter systems, media samples were taken from the both the *C. autoethanogenum*, fermenter and the *G. sulfurreducens* media 24 hour period culture. Analysis of these samples revealed that the rate of *C. autoethanogenum* bacterial cell biomass accumulation had increased to 29.3 mg dry mass/liter of fermentation media per day, a difference of 19.5 mg dry mass/liter of fermentation media per day. During this period the *G. sulfurreducens* culture degraded acetate at a rate of 1.1 g of acetate per litre per day.

Experiment 3

A *G. sulfurreducens* fermentation was initiated in 1.6 litres of media with five pooled 50 ml *G. sulfurreducens* cultures grown in media described in table 4, and table 5 (below). After an initial period of bacterial growth, exit gas from the *G. sulfurreducens* fermentation was linked to the inlet gas sparger of an established *C. autoethanogenum* fermentation. Media samples were taken from the *C. autoethanogenum* over a 24-hour period prior to the linkage of this culture with the *G. sulfurreducens* culture. Analysis of these samples revealed that the culture was accumulating bacterial cell biomass at a rate of 15.3 mg dry mass/liter of fermentation media per day. Upon linking the two fermenter systems, media samples were taken from the both the *C. autoethanogenum* fermenter and the *G. sulfurreducens* media 24 hour period culture. Analysis of these samples revealed that the rate of *C. autoethanogenum* bacterial cell biomass accumulation had increased to 103.2 mg dry mass/liter of fermentation media per day, a difference of 87.8 mg dry mass/liter of fermentation media per day. During this period the *G. sulfurreducens* culture degraded acetate at a rate of 2.1 g of acetate per litre per day.

Discussion

The impact of exit gases from a *G. sulfurreducens* fermentation oxidising acetate under electron donor limited conditions on bacterial growth by a *C. autoethanogenum* fermentation was determined. The results from the three linkage experiments presented show that exit gases from the *G. sulfurreducens* culture increased the rate of bacterial cell biomass accumulation in the *C. autoethanogenum* fermentation. Furthermore, this impact of exit gas on bacterial cell biomass accumulation in the *C. autoethanogenum* fermentation was enhanced with increasing rates of acetate degradation in the *G. sulfurreducens* culture.

More rapid accumulation of *C. autoethanogenum* bacterial cell biomass is highly desirable in the context of a commercial process for ethanol production from CO-containing gases. This is because increases in bacterial biomass accumulation allow a reduction in the time required for the bacterial concentration in a fermentation process to reach a bacterial cell density for that allows maximal process productivity per volume of input gas, per volume of reactor media. This reduction in time is associated with a concomitant reduction in operating costs and non-productive down time. Since the production of acetate by the *C. autoethanogenum* fermentation is the result of bacterial ATP biosynthesis, acetate accumulation primarily occurs during the energetically demanding growth phase of the *C. autoethanogenum* culture. Removal and remediation of acetate is thus most desirable during this period of bacterial growth.

Example 7

Impact of *Geobacter sulfurreducens* Off-Gas on Ethanol Production by *Clostridium autoethanogenum* Cultures Reaction 1: Ethanol Production by *C. autoethanogenum*

*C. autoethanogenum* was grown under anaerobic conditions in 1.6 litres of fermentation media in a 2.25 litre New Brunswick Scientific Bioflo 2000 Fermenter apparatus at 37° C. A typical media composition is described in table 1, table 2 and table 3 (below). Throughout the fermentation the input gas flow rates were established and maintained using a calibrated rotameter apparatus at atmospheric pressure. The initial input gas was a 1:1 blend of two gas mixes, the first a mix consisting of 80% $N_2$ and 20% $CO_2$ with a flow rate of 4 ml/min and the second a mix consisting of 95% CO and 5% $CO_2$ with a flow rate of 4 ml/min. The two gas streams were blended prior to being introduced into the culture media. During the linkage experiments the of 80% $N_2$ and 20% $CO_2$ gas mix was replaced with the exit gas from a *G. sulfurreducens* fermentation using acetate recovered from the *C. autoethanogenum* culture as the electron donor and sole source of carbon. To facilitate gas-liquid mass transfer the reaction media was continuously stirred at 400 rpm. Media pH was monitored using a pH Ferm probe (Broadly James Corp.) and the media Redox potential was monitored using a Redox Ferm probe (Broadly James Corp.). The output from each probe was read via a Jenco 6309POT Genco Instruments). A feedback control loop was established between the Jenco control unit and peristaltic dosing pumps (Wheaton Science Products) linked separately to acid and base buffers. Throughout the course of this experiment the fermenter media was maintained at a pH of between 5.5 and 5.8. The culture had been maintained and monitored until the population began switching in terms of metabolic output from bacterial growth and acetate production to ethanol production. The fermentation media was routinely sampled in an aseptic and anaerobic manner in order to allow a determination of ethanol, acetate and cell biomass accumulation with time.

Recovery of Acetic Acid

Accumulated acetate concentrations in the *C. autoethanogenum* culture media were maintained within a range from 5 g/l and 30 g/l throughout the culture period. To achieve this, cell-free culture media was removed from the reaction vessel via a cross-flow membrane filter (Vivaflow 200, 100,000 MWCO, PES, VivaScience). A 1.6 liter working volume was maintained in the fermentation vessel through the addition of fresh anaerobic, autoclaved media. Addition of the fresh media to the fermentation vessel was conducted under an atmosphere of 95% CO, 5% $CO_2$.

Reaction 2: Growth of *G. sulfurreducens*

*G. sulfurreducens* was grown under anaerobic conditions in 1.6 liters of fermentation media in a 2.25 liter New Brunswick Scientific Bioflo 2000 Fermenter apparatus at 35° C. *G. sulfurreducens* culture media was formulated using the acetate containing media recovered by cross-flow membrane filtration from the *C. autoethanogenum* culture. A typical media composition is described in table 4, and table 5 (below) and includes the use of a limiting concentration (20 mM) of the electron acceptor sodium fumarate. The final concentration of acetate in the media was adjusted to between 2 and 5 g/l. Throughout the fermentation the input gas flow rate was maintained at 4 ml/min through a calibrated rotameter apparatus at atmospheric pressure. The input gas composition was of 80% $N_2$ and 20% $CO_2$. The exit gas from the fermenter was either vented to the atmosphere or passed through a 0.25 µm filter and used as the input gas for the *C. autoethanogenum* containing fermenter (reaction 1 described above). The reaction media was continuously stirred at 50 rpm. Media pH was monitored using a pH Ferm probe (Broadly James Corp.). The output from each probe was read via a Jenco 6309POT (Jenco Instruments). The fermenter media was inoculated with bacteria from a number of 50 ml *G. sulfurreducens* cultures grown in the media described below (see tables 4 & 5 below), ie electron acceptor limiting media with 20 mM acetate and 20 mM fumarate. Media was enclosed in 240 mL serum bottles sealed with thick butyl rubber septa under a headspace of 80% $N_2$, 20% $CO_2$ gas mix at 10 psig. The initial pH of the fermentation media was 7.0. The fermentation media was routinely sampled in an aseptic and anaerobic manner in order to allow a determination the of acetate concentration with time.

Linkage of *G. sulfurreducens* and *C. autoethanogenum* Fermentations

Fermentations of *G. sulfurreducens* using acetate recovered from the fermentation of *C. autoethanogenum* were performed in the presence of a continuous stream of 80% $N_2$ and 20% $CO_2$ gas at a flow rate of 4 ml/min. Under electron-acceptor limiting conditions, the oxidation of acetate by *G. sulfurreducens* results in the production of $CO_2$ and $H_2$. Under these conditions, the exit gas stream from this fermentation is anticipated to contain $N_2$, $CO_2$ and $H_2$. After an initial period of bacterial growth, the exit gas stream from the *G. sulfurreducens* culture was channelled via a ⅛ inch stainless steel tubing through the input gas sparger of the *C. autoethanogenum* fermenter to replace the original of 80% $N_2$ and 20% $CO_2$ input gas at the same gas flow-rate. Care was taken throughout the linkage process to ensure that anaerobicity of both fermentations was maintained. Linkage experiments were undertaken and monitored for a 24 hour period. The impact of fermenter linkage on ethanol production in the *C. autoethanogenum* fermentation was determined by comparison with observations made under control (non-linked) conditions. All measurements described are the average data of two analyses each of two independent samples.

Figure 9:
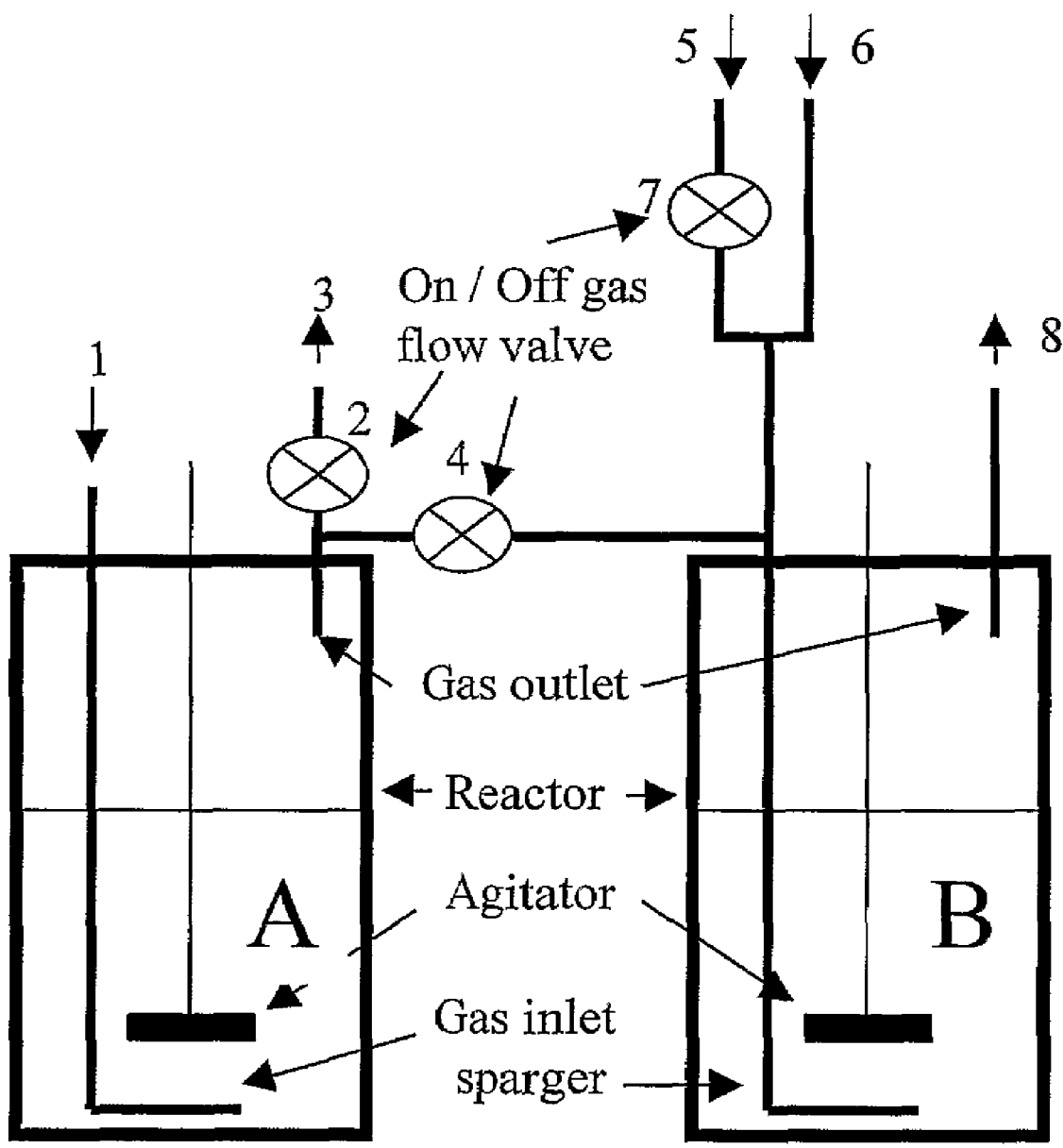

The reactor setup is shown in FIG. 9 and described below.

*G. sulfurreducens* and *C. autoethanogenum* were separately cultured in defined culture media in reactors A and B respectively. Initially, for reactor A a gas stream consisting of 80% $N_2$ and 20% $CO_2$ was introduced through gas inlet sparger 1. Initially, for reactor B a gas stream consisting of 80% $N_2$ and 20% $CO_2$ was introduced through gas inlet tube 5 and a gas stream consisting of with 95% CO and 5% $CO_2$ was introduced through gas inlet tube 6. The two gas streams were introduced as a 1:1 ratio blend. The flow rates of gases introduced into gas inlet tubes 1, 5, and, 6 were all the same, thus the overall gas flow rate through reactor B was twice that through reactor A. At this time valve 2 was open, valve 4 was closed and valve 7 was open. The gas flow rate from gas outlet 8 was recorded.

In order to determine the impact of off-gases generated in reactor A on the performance of the culture in reactor B the following actions were taken in sequence:
1. Gas flow valve 2 was closed
2. Gas flow valve 4 was opened
3. Gas flow valve 7 was closed
4. The gas flow rate from gas outlet 8 was measured and the gas inlet flow rate into reactor A through gas inlet sparger 1 was adjusted to ensure that the gas flow rate through reactor B remained constant Determination of Ethanol, Acetic Acid and Bacterial Cell Density Ethanol, acetate and bacterial growth determinations were made using the procedures described in Examples 1 to 6 above.

Results

The impact of exit gases from a *G. sulfurreducens* fermentation oxidising acetate under electron donor limited conditions on ethanol production by a *C. autoethanogenum* fermentation was determined. A *G. sulfurreducens* fermentation was initiated in 1.6 litres of media with five pooled 50 ml *G. sulfurreducens* cultures grown in media described in table 4, and table 5 (below) using an initial fumarate concentration of 5 mM. After an initial period of bacterial growth, exit gas from the *G. sulfurreducens* fermentation was linked to the inlet gas sparger of an established *C. autoethanogenum* fermentation. Media samples were taken from the *C. autoethanogenum* culture over a 24-hour period prior to the linkage of this culture with the *G. sulfurreducens* culture. The *C. autoethanogenum* culture used had become solventogenic, and was producing ethanol at a rate of 0.5 grams ethanol/dry gram bacterial biomass/liter of fermentation media/day. Upon linking the two fermenter systems, media samples were taken from the both the *C. autoethanogenum* fermenter and the *G. sulfurreducens* media over a 24 hour period. Analysis of these samples revealed that the rate of ethanol production by the *C. autoethanogenum* culture had risen to 1.9 grams ethanol/dry gram bacterial biomass/liter of fermentation media/day, a difference of 1.4 grams ethanol/dry gram bacterial biomass/liter of fermentation media/day.

Discussion

The impact of exit gases from a *G. sulfurreducens* fermentation oxidising acetate under electron donor limited conditions on ethanol production by a *C. autoethanogenum* fermentation was determined. To facilitate culture continuity and reduce the potential for any negative impacts on the *C. autoethanogenum* culture performance through an interruption in the flow of the gas stream containing CO, two input gas streams were used, one containing no CO. This gas stream was displaced during culture linkage with the off gas from the *G. sulfurreducens* culture. The results gained demonstrate the beneficial impact of off-gases produced via the degradation of acetate by *G. sulfurreducens*, in an electron donor limited environment, on the specific ethanol production rate of a *C. autoethanogenum* culture.

In the context of a commercial operation for the production of ethanol, technologies that enable an increased rate of ethanol production can have a direct, positive economic impact.

Example 8

Impact of G. sulfurreducens Off-Gas on Growth of C. autoethanogenum Cultures in a Co-Culture of C. autoethanogenum and G. sulfurreducens Experimental Procedure 15 ml liquid samples of actively growing cultures of both C. autoethanogenum and G. sulfurreducens were taken. For each sample, the bacteria were harvested and transferred into an equal volume of fresh media as described in table 6 below with the pH adjusted to 6.7. In experimental cultures a 1 ml sample of each, washed, growing bacterial sample was used to inoculate 48 ml of media (see table 6 below, pH was adjusted to 6.7). As a control, a 1 ml sample of, washed, growing C. autoethanogenum, plus 1 ml of cell free media was used to inoculate 48 ml of media. Experiments were conducted in 240 ml serum bottles in a total volume of 50 ml of liquid culture. Each bottle was sealed with a butyl rubber septum. Once inoculated, an initial 1 mL sample was taken from each serum bottle and the O.D 620, acetate concentration and ethanol concentration were determined analytically in order to describe the initial status of each culture. In addition, microscopic observation of the samples was used to confirm the appearance of each bacterial species in approximately equal concentrations in experimental cultures. Experimental and control serum bottles were filled with 95% CO and 5% $CO_2$ to a pressure of 20 PSIG. As a further CO-gas control, serum bottles inoculated with both cultures were filled with N2 gas. All serum bottles were then incubated at 35° C. shaking at approximately 150 rpm. Serum bottles were sampled regularly over a 12 day incubation period. Great care was taken throughout to maintain both ascepsis and culture anaerobicity.

Determination of Ethanol, Acetic Acid and Bacterial Cell Density

Ethanol, acetate and bacterial growth determinations were made using the procedures described in Examples 1 to 6 above.

Results

Analysis of these samples showed that after 12 days of incubation levels of bacterial cell mass accumulation in the experimental samples had risen from 3.5 mg bacterial cell dry mass per liter at the time of culture inoculation to 57.2 mg bacterial cell dry mass per liter. In co-culture control samples levels of bacterial cell mass had risen from 3.5 mg bacterial cell dry mass per liter at the time of culture inoculation to 21.0 mg bacterial cell dry mass per liter over the same time period. In CO-gas control samples levels of bacterial cell mass had risen from 3.5 mg bacterial cell dry mass per liter at the time of culture inoculation to 5.6 mg bacterial cell dry mass per liter over the same time period. This is an increase in the level of cell biomass accumulation observed in experimental co-cultures of 36.2, and 51.6 mg bacterial cell dry mass per liter over those observed in the co-culture control and the CO-gas control, respectively. Microscopic observations of culture samples confirmed that the increase in culture OD620 was primarily due to an increase in the numbers of C. autoethanogenum bacterial cells which appear morphologically distinct from G. sulfurreducens bacterial cells. All data are the average of three analyses of two independent experiments.

Discussion

These data demonstrate the advantage imparted through the co-culture of G. sulfurreducens with C. autoethanogenum on the level of biomass accumulation by the C. autoethanogenum. Biomass accumulation observed in serum bottles where C. autoethanogenum was cultured alone was less than half that observed in co-culture serum bottles containing co-cultures of C. autoethanogenum and G. sulfurreducens. Essentially no growth was observed in control co-cultures that lacked CO-gas in the headspace. These data suggest that C. autoethanogenum and G. sulfurreducens can act as a syntrophic co-culture in which C. autoethanogenum is the terminal electron acceptor allowing the oxidation of acetate by G. sulfurreducens.

More rapid accumulation of C. autoethanogenum bacterial cell biomass is highly desirable in the context of a commercial process for ethanol production from CO-containing gases. This is because increases in bacterial biomass accumulation allows a reduction in the time required for the bacterial concentration in a fermentation process to reach a bacterial cell density that allows maximal process productivity per volume of in put gas, per volume of reactor media. This reduction in time is associated with a concomitant reduction in operating costs and non-productive down time.

TABLE 1

C. autoethanogenum fermentation media

| Media Component | per L of Media |
|---|---|
| $MgCl_2 \cdot 6H_2O$ | 0.5 g |
| NaCl | 0.2 g |
| $CaCl_2$ | 0.2 g |
| $(NH_4)_2HPO_4$ | 2.0 g |
| 85% $H_3PO_4$ | 0.05 ml |
| KCL | 0.15 |
| Composite trace metal solution (LSO6) | 10 mL |
| Composite B vitamin Solution (LS03) | 1 mL |
| Resazurin (1000 mg/L stock) | 1 mL |
| $FeCL_3$ | 0.0025 g |
| Cystine HCL | 0.75 g |
| Distilled water | To 1 liter |

TABLE 2

C. autoethanogenum composite trace metal solution

| Composite trace metal solution (LS06) | per L of Stock |
|---|---|
| Nitrilotriacetic acid Or HCl 25% 7.7M 10 ml/L | 1.5 g |
| $MgSO_4 \cdot 7H_2O$ | 3.0 g |
| $MnSO_4 \cdot H_2O$ | 0.5 g |
| NaCl | 1.0 g |
| $MnCl_2 \cdot 4H_2O$ | |
| $FeSO_4 \cdot 7H_2O$ | 0.1 g |
| $Fe(SO_4)_2(NH_4)_2 \cdot 6H_2O$ | 0.8 g |
| $FeCl_2 \cdot 4H_2O$ | |
| $CoCl_2 \cdot 6H_2O$ | 0.2 g |
| $CaCl_2$ | |
| $ZnSO_4 \cdot 7H_2O$ | 0.2 g |
| $CuSO_4 \cdot 5H_2O$ | |
| $CuCl_2 \cdot 2H_2O$ | 0.02 g |
| $AlK(SO_4)_2 \cdot 12H_2O$ | 0.02 g |
| $H_3BO_3$ | 0.30 g |
| $NaMoO_4 \cdot 2H_2O$ | 0.03 g |
| *$Na_2SeO_3$ | 0.02 g |
| *$NiCl_2 \cdot 6H_2O$ | 0.02 g |
| *$Na_2WO_4 \cdot 6H_2O$ | 0.02 g |

TABLE 3

C. autoethanogenum composite B vitamin Solution

| Composite B vitamin Solution (LS03) | per L of Stock |
|---|---|
| Biotin | 20.0 mg |
| Folic acid | 20.0 mg |
| Pyridoxine hydrochloride | 10.0 mg |
| Thiamine•HCl | 50.0 mg |
| Riboflavin | 50.0 mg |
| Nicotinic acid | 50.0 mg |
| Calcium D-(*)-pantothenate | 50.0 mg |
| Vitamin B12 | 50.0 mg |
| p-Aminobenzoic acid | 50.0 mg |
| Thioctic acid | 50.0 mg |
| Distilled water | To 1 Liter |

TABLE 4

G. sulfurreducens media composition

| Media Component | per 1.0 L of Media |
|---|---|
| NH$_4$Cl | 0.25 g |
| NaH$_2$PO$_4$ | 0.60 g |
| KCl | 0.10 g |
| NaHCO$_3$ | 2.50 g |
| Wolfe's vitamin solution (LS01) | 10 mL |
| Composite mineral solution (LS06) | 10 mL |
| 2-20 mM Sodium fumarate | 0.32-3.21 g |
| Cysteine•HCL (5 mM) | 0.878 g |
| Resazurin | 0.5 mL |
| Deionised H$_2$O | To 1 L |

TABLE 5

Wolfe's Vitamin Solution

| Wolfe's Vitamin Solution | per L of Stock |
|---|---|
| Biotin | 2.0 mg |
| Folic acid | 2.0 mg |
| Pyridoxine hydrochloride | 10.0 mg |
| Thiamine•HCl | 5.0 mg |
| Riboflavin | 5.0 mg |
| Nicotinic acid | 5.0 mg |
| Calcium D-(*)-pantothenate | 5.0 mg |
| Vitamin B12 | 0.1 mg |
| p-Aminobenzoic acid | 5.0 mg |
| Thioctic acid | 5.0 mg |
| Distilled water | To 1 Liter |

TABLE 6

C. autoethanogenum fermentation media

| Media Component | per L of Media |
|---|---|
| MgCl$_2$•6H$_2$O | 0.5 g |
| NaCl | 0.2 g |
| CaCl$_2$ | 0.2 g |
| (NH$_4$)$_2$HPO$_4$ | 2.0 g |
| 85% H$_3$PO$_4$ | 0.05 ml |
| KCL | 0.15 |
| Composite trace metal solution (LSO6) | 10 mL |
| Composite B vitamin Solution (LS03) | 1 mL |
| Sodium acetate (10 mM) | 0.82 g |
| MES | 5 g |

TABLE 6-continued

C. autoethanogenum fermentation media

| Media Component | per L of Media |
|---|---|
| FeCL$_3$ | 0.0025 g |
| Cystine HCL | 0.75 g |
| Distilled water | To 1 liter |

The specific methods and compositions described herein are representative of preferred embodiments and are exemplary and not intended as limitations on the scope of the invention. Other objects, aspects and embodiments will occur to those skilled in the art upon consideration of this specification, and are encompassed within the scope and spirit of the invention. It will be readily apparent to one skilled in the art that varying substitutions and modifications may be made to the invention disclosed herein without departing from the scope and spirit of the invention. The invention illustratively described herein suitably may be practised in the absence of any element or elements, or limitation or limitations, which is not specifically disclosed herein as essential. Thus, for example, in each instance herein, in embodiments or examples of the present invention, the terms "comprising", "including", "containing" etc are to be read expansively and without limitation.

The invention claimed is:

1. A process for producing one or more alcohols from a gaseous substrate comprising CO, the process comprising the following steps:
    (a) in a bioreactor, anaerobically fermenting the gaseous substrate to produce one or more alcohols and acetate;
    (b) converting acetate obtained from step (a) into H$_2$ and CO$_2$ gases; and
    (c) using H$_2$ and/or CO$_2$ obtained from step (b) as a co-substrate in the fermentation process.

2. A process according to claim 1, wherein the one or more alcohols comprises ethanol.

3. A process according to claim 1, wherein the fermentation is carried out by one or more strains of bacteria selected from Clostridium, Moorella and Carboxydothermus.

4. A process according to claim 1, wherein the fermentation is carried out by Clostridium autoethanogenum.

5. A process according to claim 1, wherein acetate is removed from the bioreactor before the acetate is converted into H$_2$ and CO$_2$, and step (c) includes introducing either H$_2$ or a mixture of CO$_2$ and H$_2$ obtained from the acetate conversion into the bioreactor during the fermentation process.

6. A process according to claim 1, wherein step (a) is carried out in a first bioreactor and step (b) is carried out in a second bioreactor.

7. A process according to claim 1, wherein the conversion of acetate to H$_2$ and CO$_2$ is carried out by one or more strains of bacteria selected from Clostridium and Geobacter.

8. A process according to claim 1, wherein the conversion of acetate to H$_2$ and CO$_2$ is carried out by Geobacter sulfurreducens.

9. A process according to claim 1, wherein the gaseous substrate comprises a gas obtained as the result of an industrial process.

10. A process according to claim 1, wherein the gaseous substrate comprises a waste gas obtained from a steel mill.

11. A process according to claim 1, wherein acetate and the one or more alcohols are both recovered from the bioreactor before converting the acetate into H$_2$ and CO$_2$.

12. A process according to claim 1, the process further comprising, before step (a), capturing a gaseous substrate comprising CO produced as a result of an industrial process, before the gaseous substrate is released into the atmosphere.

13. The process of claim 4, wherein the fermentation is carried out by *Clostridium autoethanogenum* having all of the identifying characteristics of DSMZ deposit number DSMZ 10061.

14. The process of claim 1, wherein converting acetate into $H_2$ and $CO_2$ is carried out by microbial oxidation.

15. The process of claim 1, wherein the gaseous substrate comprises at least 70% CO and less than 15% $H_2$ by volume.

* * * * *